(12) United States Patent
Pfeffer et al.

(10) Patent No.: US 11,129,978 B2
(45) Date of Patent: Sep. 28, 2021

(54) CATHETER DEVICE

(71) Applicant: AIS GMBH AACHEN INNOVATIVE SOLUTIONS, Aachen (DE)

(72) Inventors: Joachim Georg Pfeffer, Aachen (DE); Thomas Schmitz-Rode, Aachen (DE); Rolf W. Günther, Aachen (DE)

(73) Assignee: AIS GMBH AACHEN INNOVATIVE SOLUTIONS, Aachen (DE)

(*) Notice: Subject to any disclaimer, the term of this patent is extended or adjusted under 35 U.S.C. 154(b) by 116 days.

(21) Appl. No.: 16/251,254

(22) Filed: Jan. 18, 2019

(65) Prior Publication Data

US 2019/0151522 A1 May 23, 2019

Related U.S. Application Data

(63) Continuation of application No. 14/982,870, filed on Dec. 29, 2015, now Pat. No. 10,799,624, which is a
(Continued)

(51) Int. Cl.
*A61M 1/00* (2006.01)
*A61M 60/205* (2021.01)
(Continued)

(52) U.S. Cl.
CPC .......... *A61M 60/205* (2021.01); *A61M 60/40* (2021.01); *A61M 60/419* (2021.01);
(Continued)

(58) Field of Classification Search
CPC .... A61M 1/101; A61M 1/125; A61M 1/1024; A61M 1/1036
See application file for complete search history.

(56) References Cited

U.S. PATENT DOCUMENTS 2,350,534 A 6/1944 Rosinger
3,333,127 A 7/1967 Congdon et al.
(Continued)

FOREIGN PATENT DOCUMENTS

CA 2613175 A1 1/2007
CA 2632420 A1 6/2007
(Continued)

OTHER PUBLICATIONS

Office Action issued in corresponding Canadian Application No. 3,045,168 dated Jun. 10, 2020.
(Continued)

*Primary Examiner* — Michael J D Abreu
(74) *Attorney, Agent, or Firm* — Botos Churchill IP Law LLP

(57) ABSTRACT

The catheter device comprises a motor at the proximal end of the catheter device and a drive shaft, extending from the proximal end section to the distal end section of the catheter device, for driving a rotating element located at the distal end of the catheter device. The catheter device also comprises a hose-like catheter body which encompasses the drive shaft and extends from the proximal end section to the distal end section. At the proximal end of the catheter device, the drive shaft is connected to a motor by a clutch. The clutch is a magnetic clutch with a proximal and a distal magnet unit. The proximal magnet unit is connected to the motor and the distal magnet unit to the drive shaft. The distal magnet unit is mounted fluid-tight in a clutch housing. The proximal end of the catheter body makes a fluid-tight connection with the clutch housing.

20 Claims, 26 Drawing Sheets

Related U.S. Application Data continuation of application No. 13/943,066, filed on Jul. 16, 2013, now Pat. No. 9,878,079, which is a continuation of application No. 12/211,169, filed on Sep. 16, 2008, now Pat. No. 8,489,190.

(60) Provisional application No. 60/978,256, filed on Oct. 8, 2007.

(51) Int. Cl.

| | | |
|---|---|---|
| *A61M 60/40* | | (2021.01) |
| *A61M 60/50* | | (2021.01) |
| *A61M 60/82* | | (2021.01) |
| *A61M 60/419* | | (2021.01) |
| *A61M 60/422* | | (2021.01) |
| *A61M 60/818* | | (2021.01) |
| A61B 17/3207 | | (2006.01) |
| A61M 60/135 | | (2021.01) |
| A61M 60/148 | | (2021.01) |
| A61M 60/414 | | (2021.01) |
| A61M 60/829 | | (2021.01) |

(52) U.S. Cl.
CPC .......... *A61M 60/422* (2021.01); *A61M 60/50* (2021.01); *A61M 60/818* (2021.01); *A61M 60/82* (2021.01); *A61B 17/320758* (2013.01); *A61B 2017/320775* (2013.01); *A61M 60/135* (2021.01); *A61M 60/148* (2021.01); *A61M 60/414* (2021.01); *A61M 60/829* (2021.01)

(56) References Cited

U.S. PATENT DOCUMENTS

| | | | |
|---|---|---|---|
| 3,354,833 A | 11/1967 | Laing | |
| 3,489,145 A | 1/1970 | Judson et al. | |
| 3,936,683 A | 2/1976 | Walker | |
| 4,065,234 A | 12/1977 | Yoshiyuki et al. | |
| 4,115,040 A | 9/1978 | Knorr | |
| 4,135,253 A | 1/1979 | Reich et al. | |
| 4,153,048 A | 5/1979 | Magrini | |
| 4,420,851 A | 12/1983 | Wiener | |
| 4,625,712 A | 12/1986 | Wampler | |
| 4,679,558 A | 7/1987 | Kensey et al. | |
| 4,686,982 A | 8/1987 | Nash | |
| 4,728,319 A | 3/1988 | Masch | |
| 4,747,821 A | 5/1988 | Kensey et al. | |
| 4,747,840 A | 5/1988 | Ladika et al. | |
| 4,749,376 A | 6/1988 | Kensey et al. | |
| 4,753,221 A | 6/1988 | Kensey et al. | |
| 4,777,951 A | 10/1988 | Cribier et al. | |
| 4,811,743 A | 3/1989 | Stevens | |
| 4,846,152 A | 7/1989 | Wampler et al. | |
| 4,895,557 A | 1/1990 | Moise et al. | |
| 4,919,647 A | 4/1990 | Nash | |
| 4,952,122 A | 8/1990 | Iida et al. | |
| 4,984,972 A | 1/1991 | Clausen et al. | |
| 5,011,469 A | 4/1991 | Buckberg et al. | |
| 5,017,103 A | 5/1991 | Dahl | |
| 5,037,403 A | 8/1991 | Garcia | |
| 5,042,984 A | 8/1991 | Kensey et al. | |
| 5,061,256 A | 10/1991 | Wampler | |
| 5,097,849 A | 3/1992 | Kensey et al. | |
| 5,147,186 A | 9/1992 | Buckholtz | |
| 5,158,279 A | 10/1992 | Laffey et al. | |
| 5,163,431 A | 11/1992 | Griep | |
| 5,169,378 A | 12/1992 | Figuera | |
| 5,250,059 A | 10/1993 | Andreas et al. | |
| 5,275,580 A | 1/1994 | Yamazaki | |
| 5,357,963 A | 10/1994 | Mayol et al. | |
| 5,376,114 A | 12/1994 | Jarvik | |
| 5,405,383 A | 4/1995 | Barr | |
| 5,421,338 A | 6/1995 | Crowley et al. | |
| 5,480,392 A | 1/1996 | Mous | |
| 5,527,159 A | 6/1996 | Bozeman, Jr. et al. | |
| 5,569,275 A | 10/1996 | Kotula et al. | |
| 5,678,306 A | 10/1997 | Bozeman, Jr. et al. | |
| 5,692,882 A | 12/1997 | Bozeman, Jr. et al. | |
| 5,735,792 A | 4/1998 | Vanden Hoek et al. | |
| 5,746,692 A | 5/1998 | Bacich et al. | |
| 5,749,855 A | 5/1998 | Reitan | |
| 5,766,192 A | 6/1998 | Zacca | |
| 5,776,079 A | 7/1998 | Cope et al. | |
| 5,827,171 A | 10/1998 | Dobak, III et al. | |
| 5,863,179 A | 1/1999 | Westphal et al. | |
| 5,888,241 A | 3/1999 | Jarvik | |
| 5,938,672 A | 8/1999 | Nash | |
| 5,947,892 A | 9/1999 | Benkowski et al. | |
| 5,954,745 A | 9/1999 | Gertler et al. | |
| 5,957,672 A | 9/1999 | Aber | |
| 5,964,694 A | 10/1999 | Siess et al. | |
| 6,001,078 A | 12/1999 | Reekers | |
| 6,054,788 A | 4/2000 | Dombrovski et al. | |
| 6,083,260 A | 7/2000 | Aboul-Hosn | |
| 6,116,862 A | 9/2000 | Rau et al. | |
| 6,123,725 A | 9/2000 | Aboul-Hosn | |
| 6,129,704 A | 10/2000 | Forman et al. | |
| 6,135,729 A | 10/2000 | Aber | |
| 6,183,220 B1 | 2/2001 | Ohara et al. | |
| 6,245,007 B1 | 6/2001 | Bedingham et al. | |
| 6,254,359 B1 | 7/2001 | Aber | |
| 6,413,222 B1 | 7/2002 | Pantages et al. | |
| 6,436,056 B1 | 8/2002 | Wang et al. | |
| 6,454,775 B1 | 9/2002 | Demarais et al. | |
| 6,517,528 B1 | 2/2003 | Pantages et al. | |
| 6,533,716 B1 | 3/2003 | Schmitz-Rode et al. | |
| 6,537,247 B2 | 3/2003 | Shannon | |
| 6,544,216 B1 | 4/2003 | Sammler et al. | |
| 6,841,910 B2 | 1/2005 | Gery | |
| 6,855,136 B2 | 2/2005 | Dorros et al. | |
| 6,858,001 B1 | 2/2005 | Aboul-Hosn | |
| 6,974,436 B1 | 12/2005 | Aboul-Hosn et al. | |
| 6,976,996 B1 | 12/2005 | Aboul-Hosn | |
| 6,981,942 B2 | 1/2006 | Khaw et al. | |
| 7,022,100 B1 | 4/2006 | Aboul-Hosn et al. | |
| 7,027,875 B2 | 4/2006 | Siess et al. | |
| 7,179,291 B2 | 2/2007 | Rourke et al. | |
| 7,393,181 B2 | 7/2008 | McBride et al. | |
| 7,646,376 B2 | 1/2010 | Blersch | |
| 7,731,675 B2 | 6/2010 | Aboul-Hosn et al. | |
| 7,841,976 B2 | 11/2010 | McBride et al. | |
| 7,927,068 B2 | 4/2011 | McBride et al. | |
| 8,079,948 B2 * | 12/2011 | Shifflette | F04D 29/382 600/16 |
| 8,439,859 B2 | 5/2013 | Pfeffer et al. | |
| 8,489,190 B2 | 7/2013 | Pfeffer et al. | |
| 8,888,728 B2 | 11/2014 | Aboul-Hosn et al. | |
| 9,138,518 B2 | 9/2015 | Campbell et al. | |
| 2001/0000528 A1 | 4/2001 | Cho | |
| 2002/0151799 A1 | 10/2002 | Pantages et al. | |
| 2003/0135086 A1 | 7/2003 | Khaw et al. | |
| 2003/0135940 A1 | 7/2003 | Lev et al. | |
| 2003/0149473 A1 | 8/2003 | Chouinard et al. | |
| 2003/0187322 A1 | 10/2003 | Siess | |
| 2003/0208097 A1 | 11/2003 | Aboul-Hosn et al. | |
| 2004/0022640 A1 | 2/2004 | Siess et al. | |
| 2004/0044266 A1 | 3/2004 | Siess et al. | |
| 2004/0113502 A1 | 6/2004 | Li et al. | |
| 2004/0193046 A1 | 9/2004 | Nash et al. | |
| 2004/0260237 A1 | 12/2004 | Squadrito | |
| 2005/0135942 A1 | 6/2005 | Wood et al. | |
| 2005/0137680 A1 | 6/2005 | Ortiz et al. | |
| 2006/0008349 A1 | 1/2006 | Khaw | |
| 2006/0041277 A1 | 2/2006 | Deem et al. | |
| 2006/0062672 A1 | 3/2006 | McBride et al. | |
| 2006/0155312 A1 | 7/2006 | Levine et al. | |
| 2006/0195004 A1 | 8/2006 | Jarvik | |
| 2007/0118072 A1 | 5/2007 | Nash | |
| 2008/0103591 A1 | 5/2008 | Siess | |
| 2008/0114339 A1 | 5/2008 | McBride et al. | |
| 2008/0132747 A1 | 6/2008 | Shifflette | |
| 2008/0183136 A1 | 7/2008 | Lenker et al. | |
| 2009/0060743 A1 | 3/2009 | McBride et al. | |

(56) References Cited

U.S. PATENT DOCUMENTS

| | | |
|---|---|---|
| 2009/0062597 A1 | 3/2009 | Shifflette |
| 2009/0088609 A1 | 4/2009 | Schmitz-Rode et al. |
| 2009/0093764 A1 | 4/2009 | Pfeffer et al. |
| 2009/0093796 A1 | 4/2009 | Pfeffer et al. |
| 2009/0218728 A1 | 9/2009 | Moyer |
| 2009/0227892 A1 | 9/2009 | Krombach et al. |
| 2010/0210895 A1 | 8/2010 | Aboul-Hosn et al. |
| 2010/0268017 A1 | 10/2010 | Siess |
| 2011/0071338 A1 | 3/2011 | McBride et al. |
| 2013/0066139 A1 | 3/2013 | Wiessler et al. |
| 2013/0066140 A1 | 3/2013 | McBride et al. |
| 2013/0204068 A1 | 8/2013 | Gnanashanmugam et al. |
| 2013/0345492 A1 | 12/2013 | Pfeffer et al. |
| 2015/0073202 A1 | 3/2015 | Aboul-Hosn et al. |
| 2016/0089482 A1 | 3/2016 | Siegenthaler |
| 2016/0106896 A1 | 4/2016 | Pfeffer et al. |
| 2016/0106898 A1 | 4/2016 | Pfeffer et al. |
| 2016/0136341 A1 | 5/2016 | Pfeffer et al. |
| 2016/0136342 A1 | 5/2016 | Pfeffer et al. |

FOREIGN PATENT DOCUMENTS

| | | | |
|---|---|---|---|
| DE | 4414903 A1 | 11/1995 | |
| DE | 10059714 C1 | 5/2002 | |
| DE | 11200400180 T5 | 11/2006 | |
| DE | 102005039950 A1 | 3/2007 | |
| EP | 0364293 A2 | 4/1990 | |
| EP | 0445782 A1 | 9/1991 | |
| EP | 0764448 A2 | 3/1997 | |
| EP | 0768900 A1 | 4/1997 | |
| EP | 0847767 A1 | 6/1998 | |
| EP | 0914171 A2 | 5/1999 | |
| EP | 0916359 A1 | 5/1999 | |
| EP | 1034808 A1 | 9/2000 | |
| EP | 1207934 A2 | 5/2002 | |
| EP | 1207935 A1 | 5/2002 | |
| EP | 1207936 A1 | 5/2002 | |
| EP | 2047872 A1 | 4/2009 | |
| EP | 2047873 A1 | 4/2009 | |
| EP | 2229965 A1 | 9/2010 | |
| EP | 2298374 A1 | 3/2011 | |
| EP | 3 000 493 | 3/2016 | |
| EP | 3000492 A1 | 3/2016 | |
| FR | 2788223 A1 | 7/2000 | |
| JP | H04126158 A | 4/1992 | |
| WO | WO-88/09874 | 12/1988 | |
| WO | WO-8904644 A1 | 6/1989 | |
| WO | WO-1997039698 | 10/1997 | |
| WO | WO-9944651 A1 * | 9/1999 | ........... F04D 29/242 |
| WO | WO-1999044651 | 9/1999 | |
| WO | WO-1999058170 | 11/1999 | |
| WO | WO-2000019097 A1 | 4/2000 | |
| WO | WO-2000043053 A1 | 7/2000 | |
| WO | WO-2001083016 A2 | 11/2001 | |
| WO | WO-2002022200 A1 | 3/2002 | |
| WO | WO-2002043791 A1 | 6/2002 | |
| WO | WO-2003103745 A2 | 12/2003 | |
| WO | WO-2005030296 A2 | 4/2005 | |
| WO | WO-2006020942 A1 | 2/2006 | |
| WO | WO-2006034158 A2 | 3/2006 | |
| WO | WO-2006051023 A1 | 5/2006 | |
| WO | WO-2006111954 A2 | 10/2006 | |
| WO | WO-2007003351 A1 | 1/2007 | |
| WO | WO-2007112033 A2 | 10/2007 | |
| WO | WO-2009046789 A1 | 4/2009 | |
| WO | WO-2010063494 A1 | 6/2010 | |

OTHER PUBLICATIONS

Certified Copy of U.S. Appl. No. 60/785,299, filed Mar. 23, 2006.
JOMED GmbH, Marketing-Broshure: JOMED Reitan Catheter Pump (6 pages).
JOMED Implantate GmbH, Handelsregister-Abt. B-des Amtsgerichts (4 pages).
JOMED Catheter PumpTM: Minimally Invasive Cardiac Assist (6 pages).
Mizuguschi et al., "Development of the Baylor/NASA Axial Flow Ventricular Assist Device: In Vitro Performance and Systematic Hemolysis Test Results," Artificial Organs, vol. 18(1): 32-43 (1994).
Reitan, "Evaluation of a New Percutaneous Cardiac Assist Device," Dissertation, Lund University 2002 (172 pages).
Thoratec Europe Limited and AIS GMBH High Court Justice Case No. HP02015-000035 (53 pages) (2016).
Urteil des Bundespatentgerichts BPatG 4 Ni 25/15 (EP) (48 pages) (2017).
Urteil des Bundespatentgerichts BGatG 4Ni25/15 (EP) (37 pages) (2017).
U.S. Appl. No. 60/610,938, filed Sep. 18, 2005, McBride et al.
U.S. Appl. No. 60/785,531, filed Mar. 23, 2006, Campbell et al.
U.S. Appl. No. 60/785,299, filed Mar. 23, 2006, McBride et al.
Brochure Impella Pumpsystem of Impella CardioSystems AG, "Turning Lives Around," Aug. 2003 (4 pages).
Buecker et al., "Use of a Nonmetallic Guide Wire for Magnetic Resonance—Guided Coronary Artery Catheterization," Investigative Radiology 39(11):656-660 (2004).
Brücker, Ch. et al., "Flow Technological Design and Optimization of Percutaneously Implanstagexx Micro Blood Pump," Biomedizinische Technik, vol. 47; Supplemental Issue 1: 114-117 (2002). (Translation).
Compendium of Technical and Scientific Information for the Hemopump Temporary Cardiac Assist System, 1988 (15 pages).
Dekker, et al, "Efficacy of a New Intraaortic Propeller Pump vs the Intraaortic Balloon Pump," Chest Journal, 123(6):2089-2095 (2003) (7 pages).
Frazier, et al, "First Human Use of the Hemopump, A Catheter-Mounted Ventricular Assist Device," Annals of Thoracic Surgery, 49(2):299-304 (1990).
International Preliminary Report on Patentability, from PCT/EP09/008858, dated Jun. 7, 2011 (5 pages).
JOMED Reitan Catheter Pump Brochure, www.jomed.com/rcp (undated) (6 pages).
Lueger, Lexikon der Technik, "Lexikon der Feinwerktechnik", vol. 13, Deutsche Verlags-Anstalt GmbH, Stuttgart, seite 551 (1968) (4 pages) (non-translated).
Reitan, et al, "Hydrodynamic properties of a new percutaneous intra-aortic axial flow pump," ASAIO Journal, 46(3):323-329 (2000).
Rothman, Martin T, "The Reitan Catheter Pump: A New Versatile Approach for Hemodynamic Support," London Chest Hospital Barts & the Long NHS Trust, presented at TCT Conference, Oct. 24-26, 2006, (40 pages).
Schmitz-Rode, et al., "Axial Flow Catheter Pump for Circulatory Support," Biomedizinische Technik, Bank 47, Erganzungsband 1, Teil 1, pp. 142-143 (2002).
Schmitz-Rode, et al., "An Expandable Percutaneous Catheter Pump for Left Ventricular Support," Journal of the American College of Cardiology, 45(11):1856-1861 (2005).
Schmitz-Rode, et al., "Temporary Pulmonary Stent Placement as Emergency Treatment of Pulmonary Embolism," Journal of the American College of Cardiology, 48(4):812-816 (2006).
Schmitz-Rode, T., "Perkutan implantierbare, selbstentfaltbare Linksherz-Unterstützungspumpe," Berichte aus der Medizintechnik, Manfred Weck (Hrsg.), 3. Symposium: Neue Technologien für die Medizin, Shaker Verlag, 2001, S. 393-404; Schmitz-Rode, T., "Percutaneously implantable, self-deploying left heart support pump," Medical Engineering Report, Manfred Weck (Ed.): 393-404 (13 pages total) (2001).
Siess and Reul, "Basic Design Criteria for Rotary Blood Pumps," H. Matsuda, Rotary Blood Pumps, Springer, Japan: 69-83 (2000).
Siess, et al., "Concept, Realization, and First in Vitro Testing of an Intraarterial Microaxial Blood Pump," Artificial Organs, vol. 19(7): 644-652 (1995).
Siess, et al., "From a Lab Type to a Product: A Restrospective View of Impella's Assist Technology," Artificial Organs, vol. 25(5): 414-421 (2001).
Siess, et al., "Hydraulic refinement of an intraarterial microaxial blood pump," The International Journal of Artificial Organs, vol. 18(5): 273-285 (1995).

(56) References Cited

OTHER PUBLICATIONS

Siess, Thorsten, "Systems Analysis and Development of Intravascular Rotation Pumps for Heart Support," Helmholtz-Institut for Biomedical Technology: 199 pages (1998).
Siess, T. "System Analysis and Development of Intravascular Rotation Pumps for Cardiac Assist," Helmholtz-Institute Jun. 24, 1998 (105 pages) and partial English translation (37 pages) (144 pages total).
Verma, et al., "Evaluation of a Newly Developed Percutaneous Thrombectomy Basket Device in Sheep with Central Pulmonary Embolisms," Investigative Radiology, 41(10):729-734 (2006).
Wampler, et al., "In vivo evaluation of a peripheral vascular access axial flow blood pump," ASAIO Transactions, 34(3):450-454 (1988).
Nullity action filed by Thoratec Europe Limited against German part of DE 50 2007 005 015.6 of EP Patent No. EP 2 047 872 B1 dated Dec. 14, 2020 (77 pages), with English translation.

\* cited by examiner

CATHETER DEVICE

CROSS REFERENCE TO RELATED APPLICATIONS

This application is a continuation of U.S. patent application Ser. No. 14/982,870, filed on Dec. 29, 2015, now U.S. Pat. No. 10,799,624, which is a continuation of U.S. patent application Ser. No. 13/943,066, filed on Jul. 16, 2013, now U.S. Pat. No. 9,878,079, which is a continuation application of U.S. patent application Ser. No. 12/211,169 filed on Sep. 16, 2008, now U.S. Pat. No. 8,489,190, which in turn claims priority to U.S. Provisional Application No. 60/978,256 filed in the United States Patent and Trademark Office on Oct. 8, 2007, the contents of all of which are hereby incorporated by reference herein in their entirety for all purposes.

BACKGROUND OF THE INVENTION

Technical Field

The invention relates to a catheter device, in particular a catheter device with an elongated drive shaft.

Related Art

Implantable blood pumps are used increasingly in the treatment of patients with serous heart conditions. Such blood pumps have so far been provided mainly for long-term use. However, blood pumps are also being developed which are designed for short-term support for the heart and may be inserted by minimally invasive means. Here the medical objectives are stress-relief for and recovery of the heart, or to provide bridging until a possible heart transplant. The range of application of such pumps depends on the one hand on the simplicity of inserting them into the body, and on the other hand on the feasible technical properties, in particular the reliable operating life of the available pump systems which may be obtained. Ideally it should be possible to insert such a blood pump for short-term treatment by percutaneous-intravascular means without any surgical intervention.

In cardiogenic shock, the ejection performance of the left ventricle is considerably reduced. The reduced coronary supply can lead to irreversible heart failure. Through the use of a temporary left-ventricular support system, the pump function of the left ventricle should be partly or largely taken over and the coronary supply improved. In heart operations such a system may be used for both left and right ventricles and may replace a heart-lung machine.

A percutaneous-intravascular system which has to date been of clinical importance is the intra-aortal balloon pump (IABP). The intra-aortal balloon pump or intra-aortal counter-pulsation is a mechanical system, also used to support the pumping performance of the heart in patients with cardiogenic shock. This involves a catheter with a cylindrical plastic balloon being pushed ahead via the groin into the thoracic aorta (aorta thoracalis), so that the balloon lies below the outlet of the left clavicular artery (arteria subclavia sinistra). There the balloon is blown is inflated rhythmically by an external pump with every heart action in diastole with 30-40 cm3 helium and deflated in systole. In this way the balloon pump improves the blood supply to the heart muscle and also that of all other organs. The obtainable haemodynamic improvement is however very limited since, on account of the construction principle of the IABP, no active blood delivery takes place. Through counter-pulsation only the aorta is closed below the left ventricle in the rhythm of the heartbeat, so that the blood still discharged by the heart is pressed back and redistributed, also in the coronaries. There is no increase in blood flow.

A known transfemoral implantable micro axial pump, "Hemopump™" of the company Medtronic Inc., USA, represents after experimental and preliminary clinical testing a promising concept for effecting adequate relief of systemic heart strain. The intake nozzle of the pump is placed in the left ventricle retrogressively via the aortic valve. The pump rotor is located at the end of a cannula in the upper aorta descendens and is driven by an external motor. The disadvantage of the system is that the transfemoral implantation, due to the large diameter of the rotor, is possible only through an operation involving a femoral arteriotomy and if necessary by a graft coupling.

WO 99/44651 discloses an axial pump which may be introduced via the blood vessel system of a patient. The axial pump has a flexible, compressible tube which forms the pump housing. In the tube is a radially compressible rotor. The drive shaft of the rotor runs through a catheter. Together with the tube and the rotor, the catheter may be drawn into a cover hose. The radial compressibility of the components makes it possible to realise a small puncture diameter suitable for percutaneous implantation by the Seldinger technique. Through the unfolding in the heart vessel system, a relatively large pump diameter of 10 to 14 mm may be provided. This reduces the rotor speed and therefore the mechanical stress on the components.

Described in U.S. Pat. No. 4,753,221 is a catheter with an integrated blood pump which has folding blades. The blood pump is an axial pump provided with a balloon at its end. The balloon can be pumped up to unfold the pump jacket and to close the flow path leading past the pump, so fixing the pump in the blood vessel. In a further embodiment it is provided that a cup-shaped end of the catheter is arranged in a tubular guide catheter which is then withdrawn so as to unfold the cup-shaped end.

DE 10 059 714 C1 discloses an intravascular pump. The pump has a drive section and a pump section which are so small in diameter that they can be pushed through a blood vessel. A flexible cannula adjoins the pump section. To reduce flow resistance, the cannula may be expanded to a diameter which exceeds that of the drive section and pump section respectively. So that the pump may be introduced into the body by the Seldinger technique involving punctures in the blood vessel, the cannula is constricted, in which state it has a smaller diameter. In the blood vessel it is expanded so as to offer less flow resistance to the blood to be pumped.

Described in JP 4126158 and EP 0 445 782 A1 respectively is an artificial heart for implantation in the body. The artificial heart has a pump section and a drive section for driving the pump section. The pump section is relatively small and serves to accommodate an axial flow pump in the form of a screw pump. Different types of screw pump are provided.

Described in EP 0 364 293 A2 is a catheter with integral blood pump. A flexible edge extends over a tubular section of the catheter and contacts the wall of the aorta, ensuring by this means that all the blood within the aorta flows through the pump. In addition the flexible, expandable edge provides clearance between the pump and the aortic valve.

SUMMARY OF THE INVENTION

The present invention is based on the problem of creating a catheter device with a drive shaft extending over virtually the whole catheter device and which may be driven reliably at high speed.

The catheter device comprises a motor located at the proximal end of the catheter device and a drive shaft, extending from the proximal end section to the distal end section of the catheter device, for driving a rotating element located at the distal end of the catheter device. At the proximal end of the catheter device, the drive shaft is connected to a motor by a clutch. The clutch is a magnetic clutch with a proximal and a distal magnet unit. The proximal magnet unit is connected to the motor and the distal magnet unit to the drive shaft. The distal magnet unit is supported in a clutch housing and physically separated from the proximal magnet unit by a wall.

Because of the separation of the output-side clutch element up to the distal end of the catheter device, it is not necessary to guide the drive shaft to the outside via a hole. Any such feed-through would require sealing, but such sealing limits the speed. Since this catheter device has no corresponding sealing of a drive shaft feed-through, very high speeds may be transmitted to the drive shaft.

The contribution of the transmittable torque is limited by the magnet ring bearing and the magnetic connection of the two magnet units. As soon as the settable torque is exceeded, the two magnet units separate.

Preferably the catheter device comprises a hose-like catheter body which encompasses the drive shaft and extends from the proximal end section to the distal end section of the catheter device. The catheter body has a fluid-tight connection with the clutch housing.

Via a rinsing bore in the clutch housing it is possible to introduce a rinsing medium to lubricate the drive shaft and the output-side clutch element. This prevents blood from penetrating into the area between the drive shaft and the catheter body, and impairing the rotatability of the drive shaft.

Preferably an output-side clutch element carrying the distal magnet unit is supported by a sliding bearing. By this means the distance between the two magnet units may be set precisely.

In accordance with a development, an additional magnet ring bearing is provided. On the one hand this provides further and especially radial support for the output-side clutch element, and on the other hand it is able to counteract the forces exerted by the magnet units, so that the force with which the output-side clutch element is pressed against the sliding bearing is reduced.

The maximum torque transferable by the magnetic clutch is determined by both the distance between the two magnet units set by the sliding bearing and by the force with which the magnet ring bearing acts on the clutch element in the axial direction.

The diameter of the drive shaft may lie in the range from 0.3 mm to 1 mm and is preferably around 0.4 mm to 0.6 mm. The smaller the diameter of the drive shaft, the greater can be the speed at which the drive shaft is driven by the motor.

The element rotating due to the drive shaft may be a rotor, a milling tool or another tool.

Such a rotor is preferably designed to unfold automatically. It may be provided with a pump housing which, like the rotor, is compressible to a small diameter. According to a preferred embodiment, the rotor and the pump housing are made of a memory material.

The combination of an automatically unfolding pump head with the magnetic clutch explained above forms a catheter device with which one the one hand, owing to the high speed and the large rotor, a high pump performance is obtained, and on the other hand a high life expectancy of several hours to several days is achieved.

Other features and advantages of the invention will be apparent from the following detailed description, drawings and claims

DETAILED DESCRIPTION OF THE INVENTION

FIG. 1. shows a perspective view of a catheter device according to the invention.

FIG. 2. shows an exploded drawing of a catheter device according to the invention.

FIG. 3. shows a body cap of the catheter device shown cut away at the side.

FIG. 4. shows a distal catheter body element of the catheter device in a cut-away side view.

FIG. 5. shows a connection bush of the catheter device in a cut-away side view.

FIG. 6. shows a pump of the catheter device with support in a cut-away side view.

Figure 8:
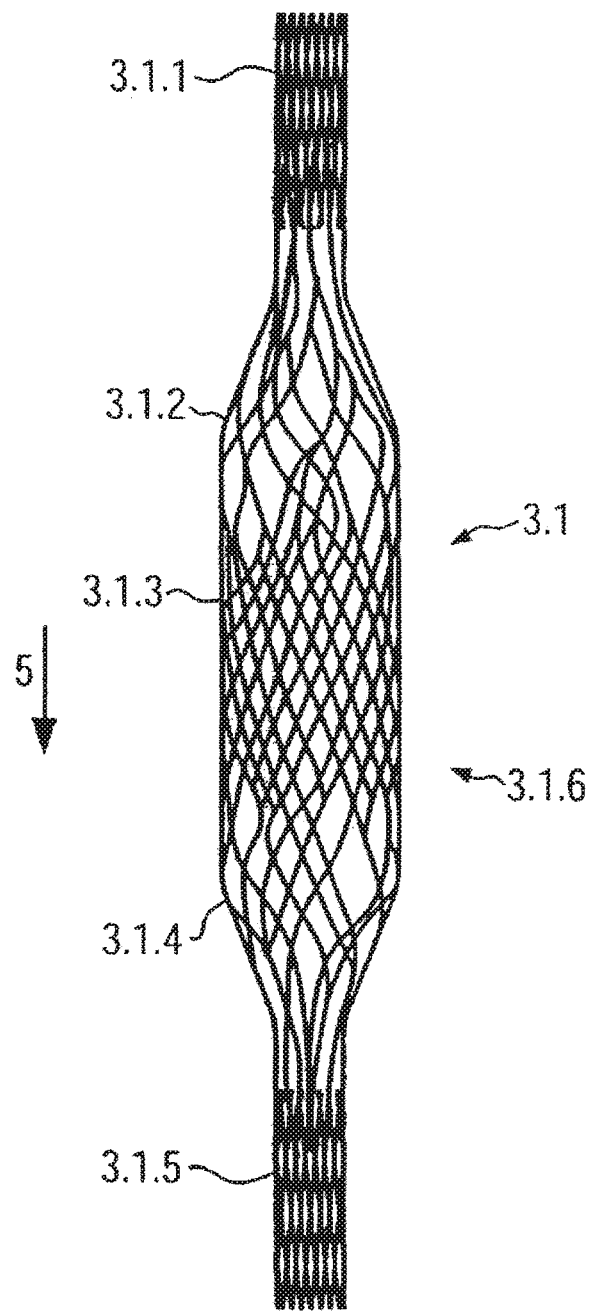

FIG. 8. shows a mesh structure of a pump housing of the catheter device.

Figure 9:
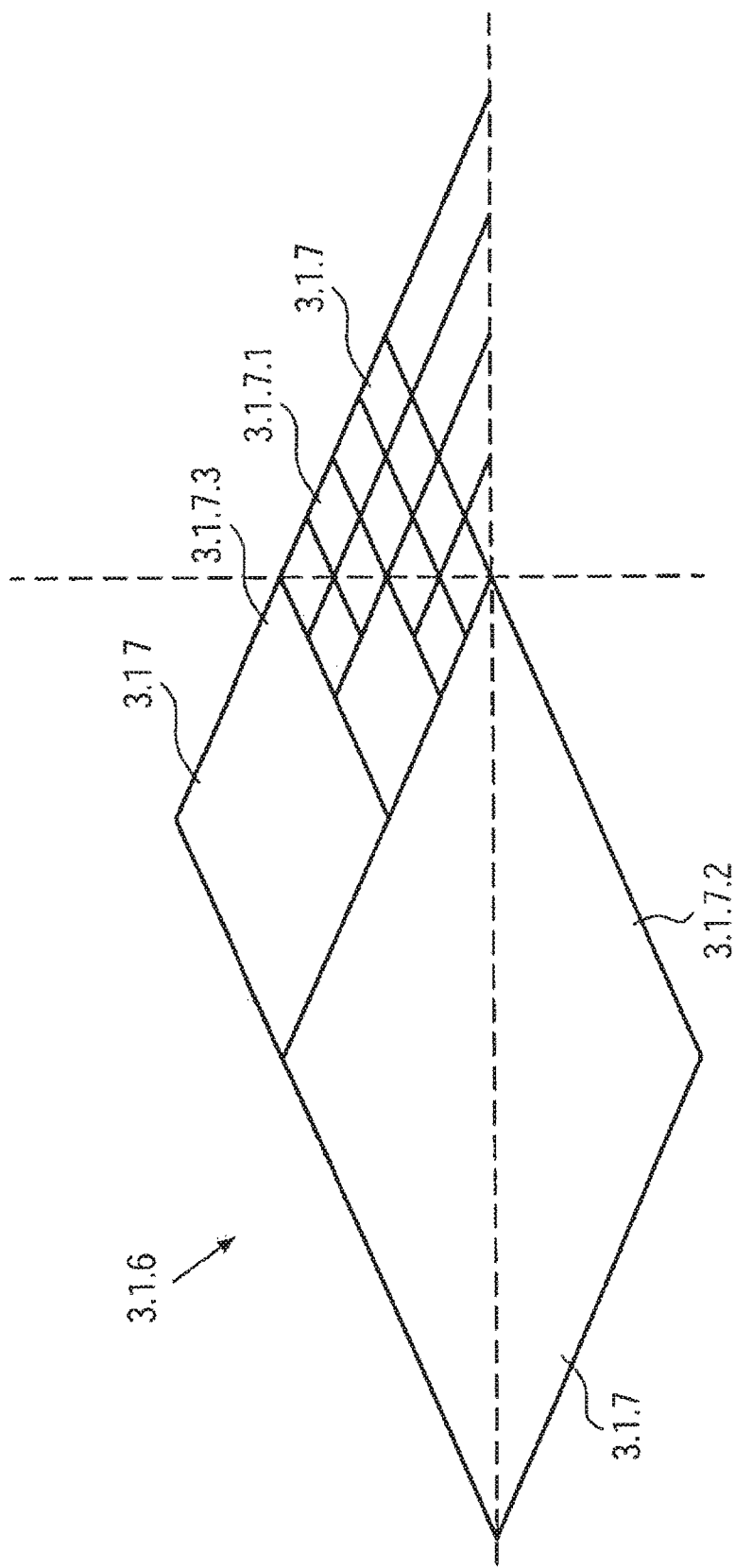

FIG. 9. shows a detail of the mesh structure of the pump housing of the catheter device.

Figure 10:
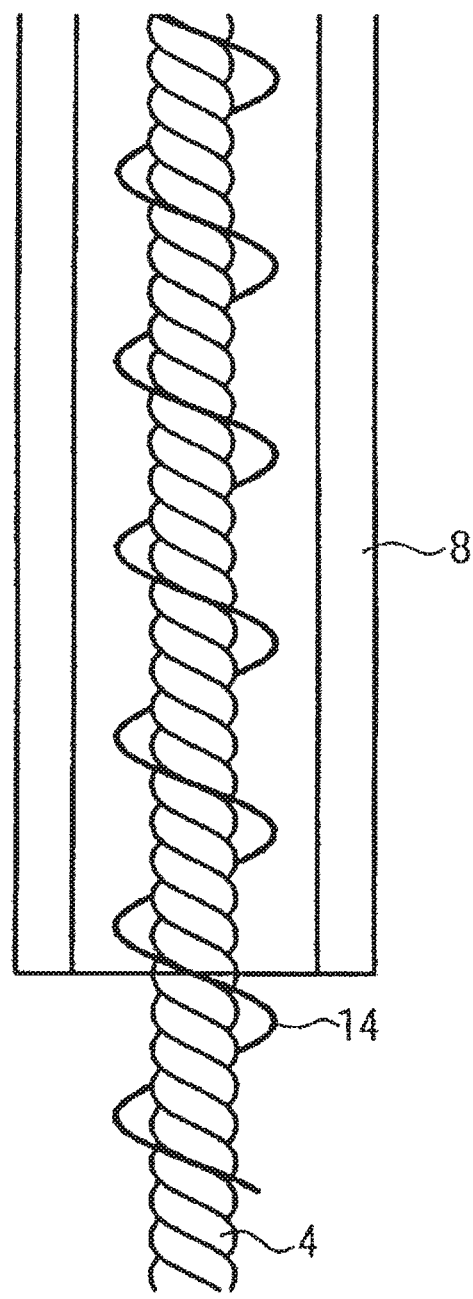

FIG. 10. shows a drive shaft with guide spiral and shaft protector of the catheter device.

Figure 11A:
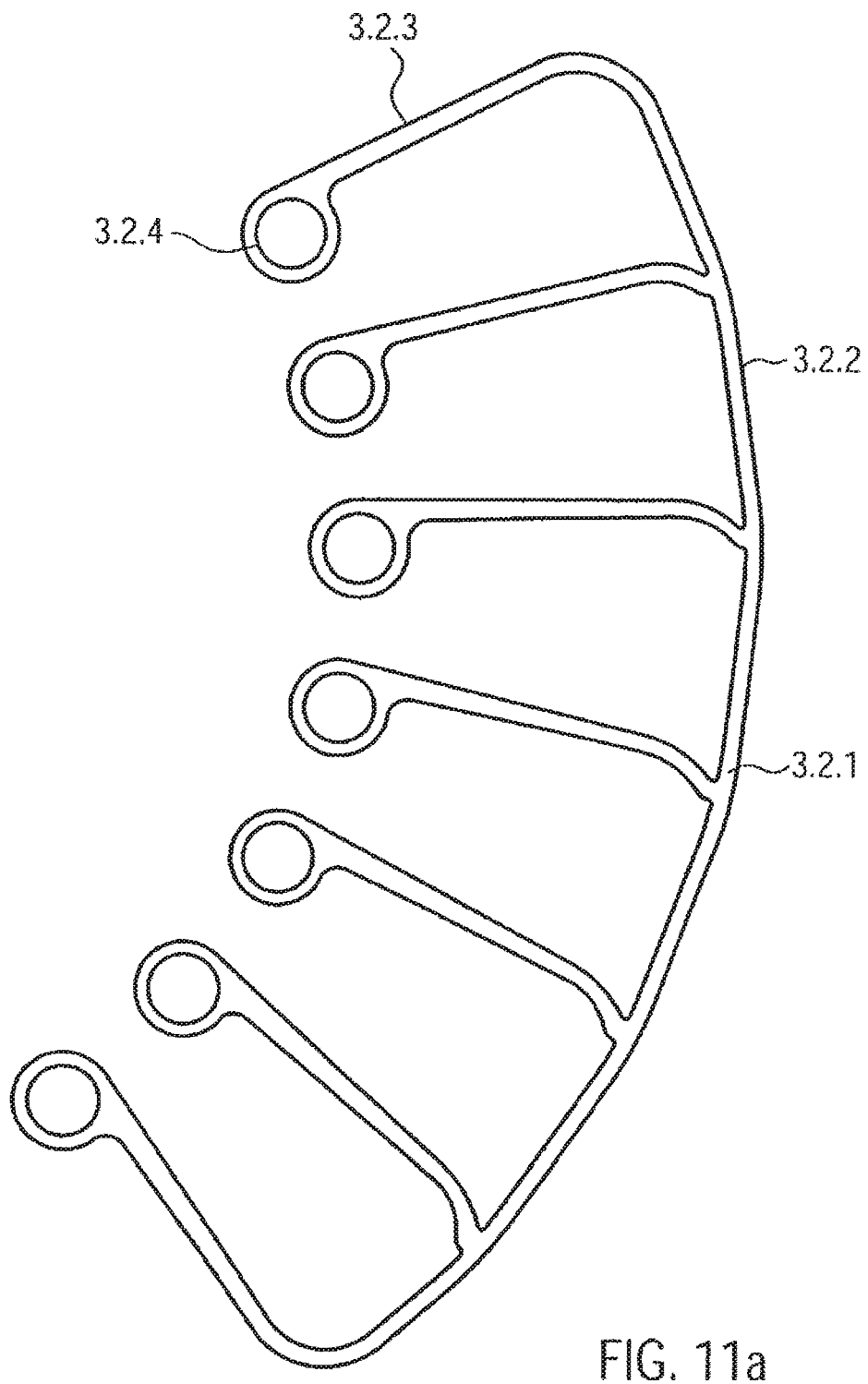

FIG. 11A shows a frame structure of a rotor of a pump of the catheter device.

Figure 11B:
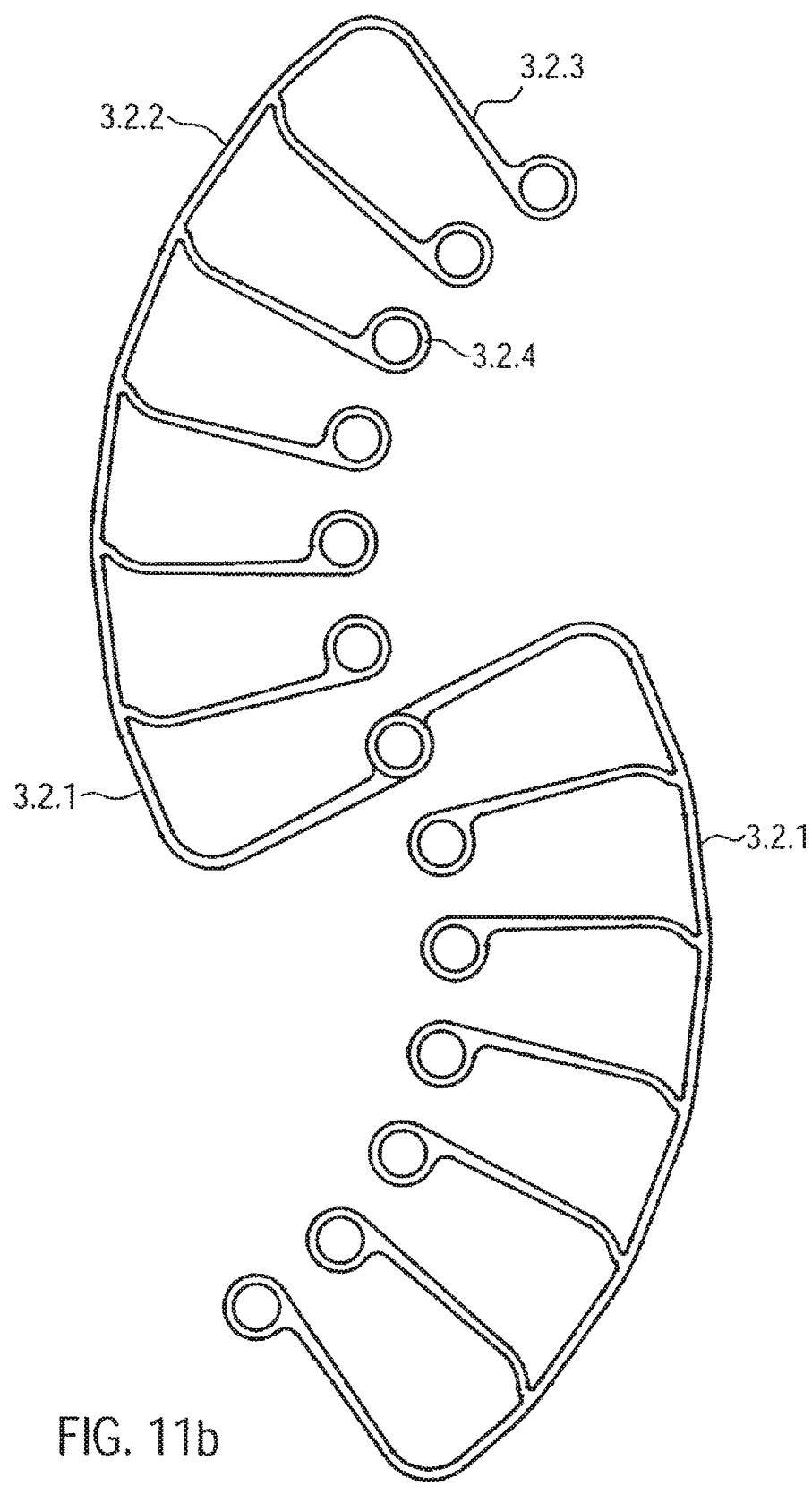

FIG. 11B shows a further frame structure of the rotor of the pump of the catheter device.

Figure 12:
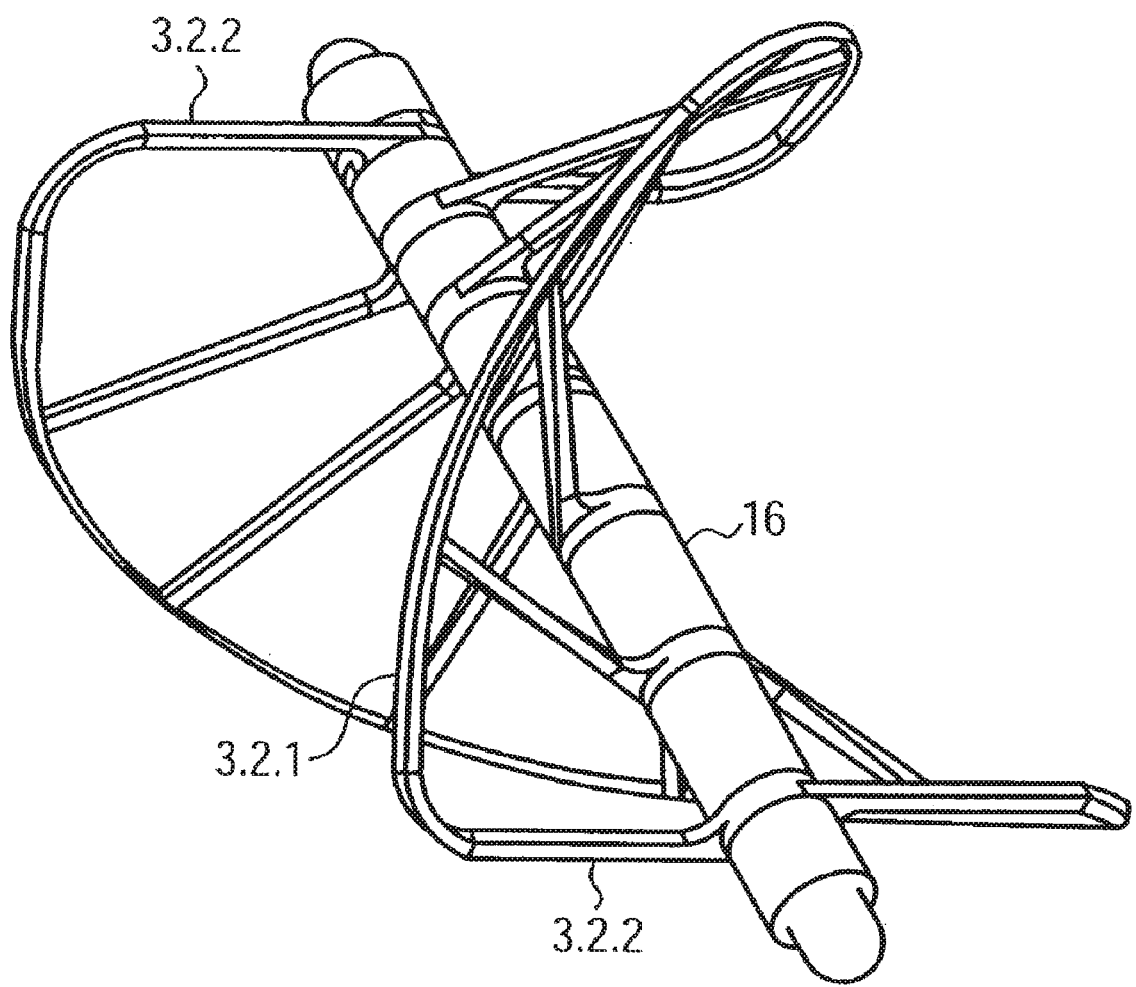

FIG. 12. shows the rotor according to the invention of the pump of the catheter device in a perspective view.

Figure 13:
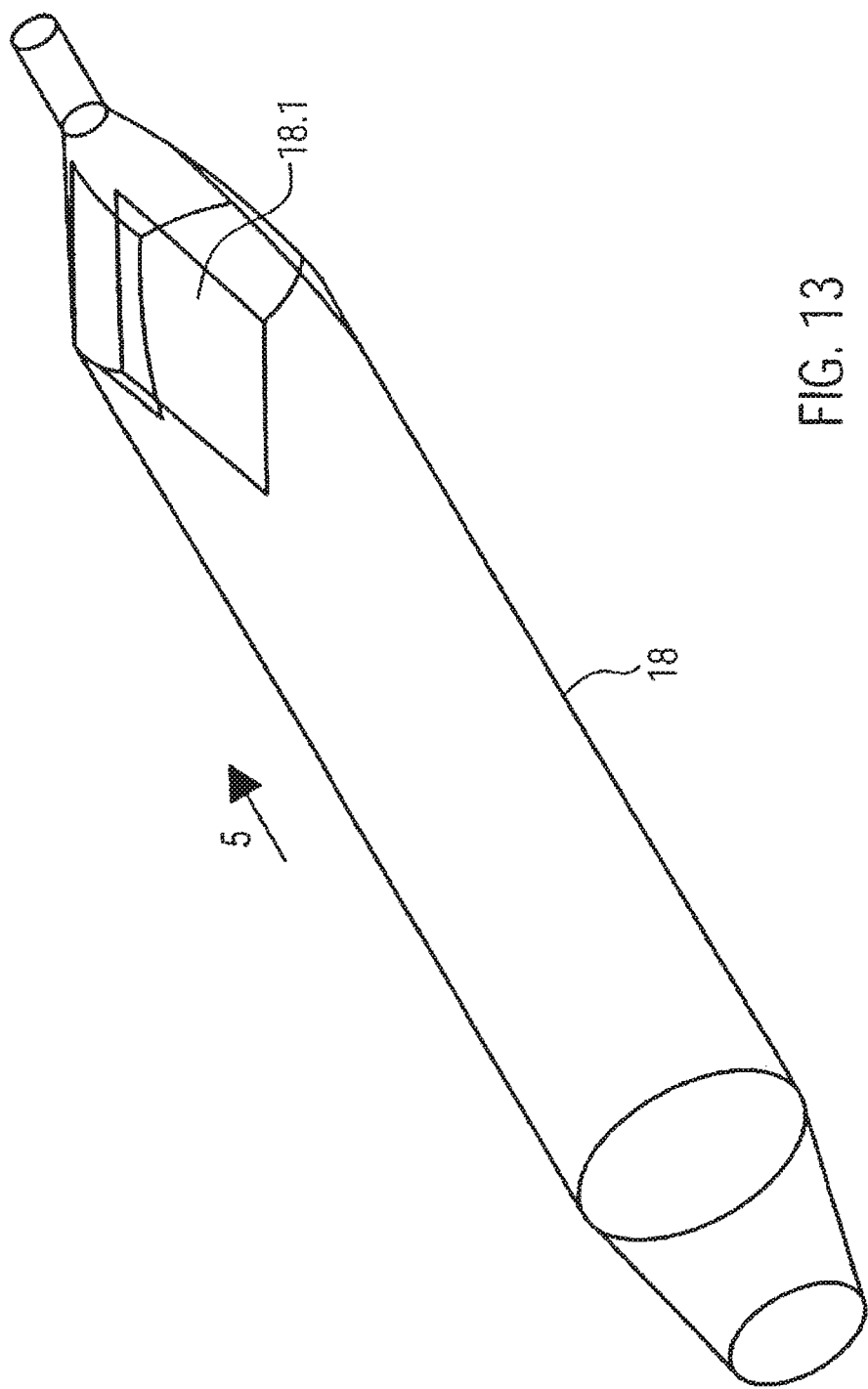

FIG. 13. shows an outlet hose of the catheter device in a perspective view.

Figure 14:
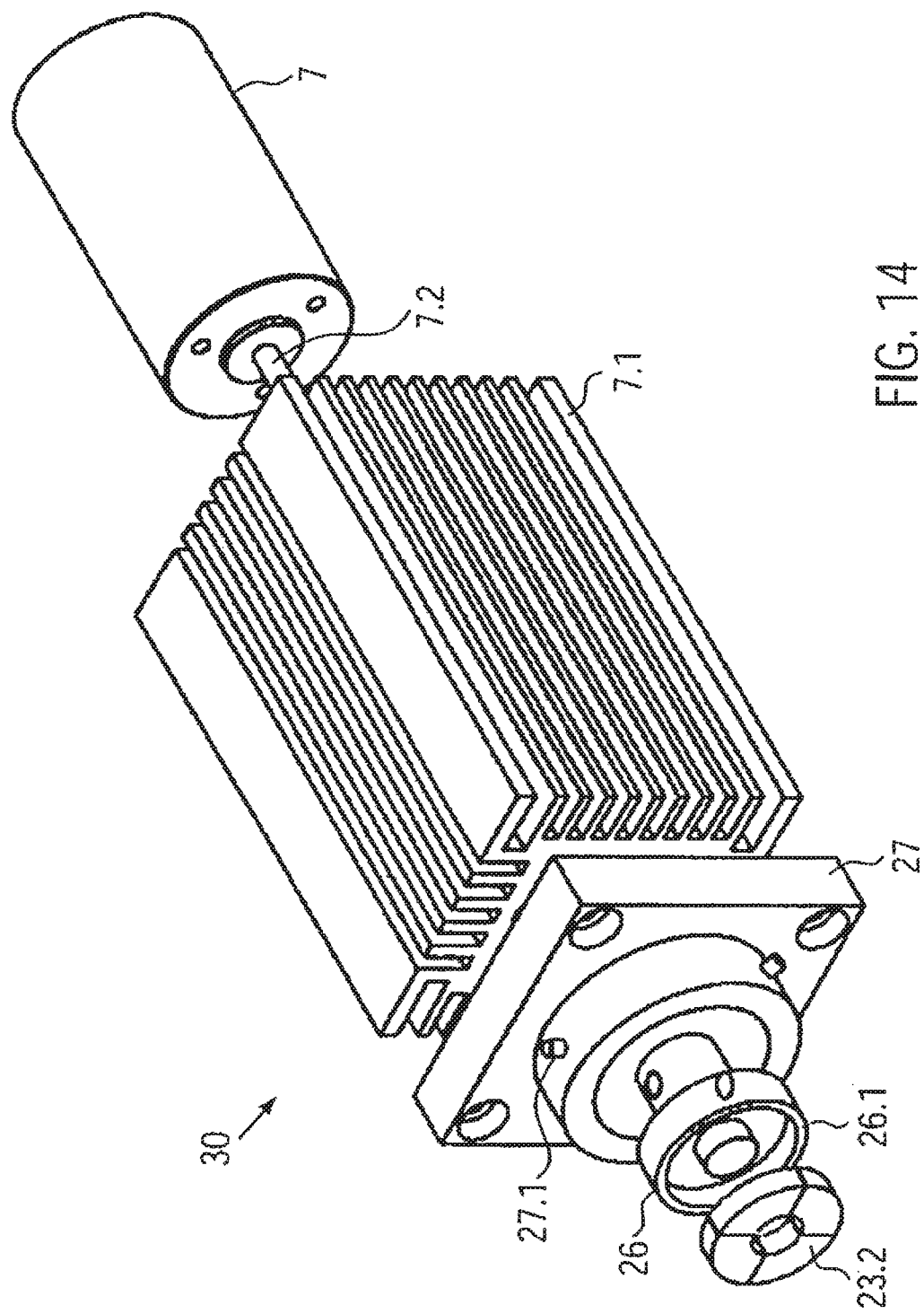

FIG. 14. shows a clutch according to the invention with clutch housing and motor of the catheter device in a perspective view.

Figure 15:
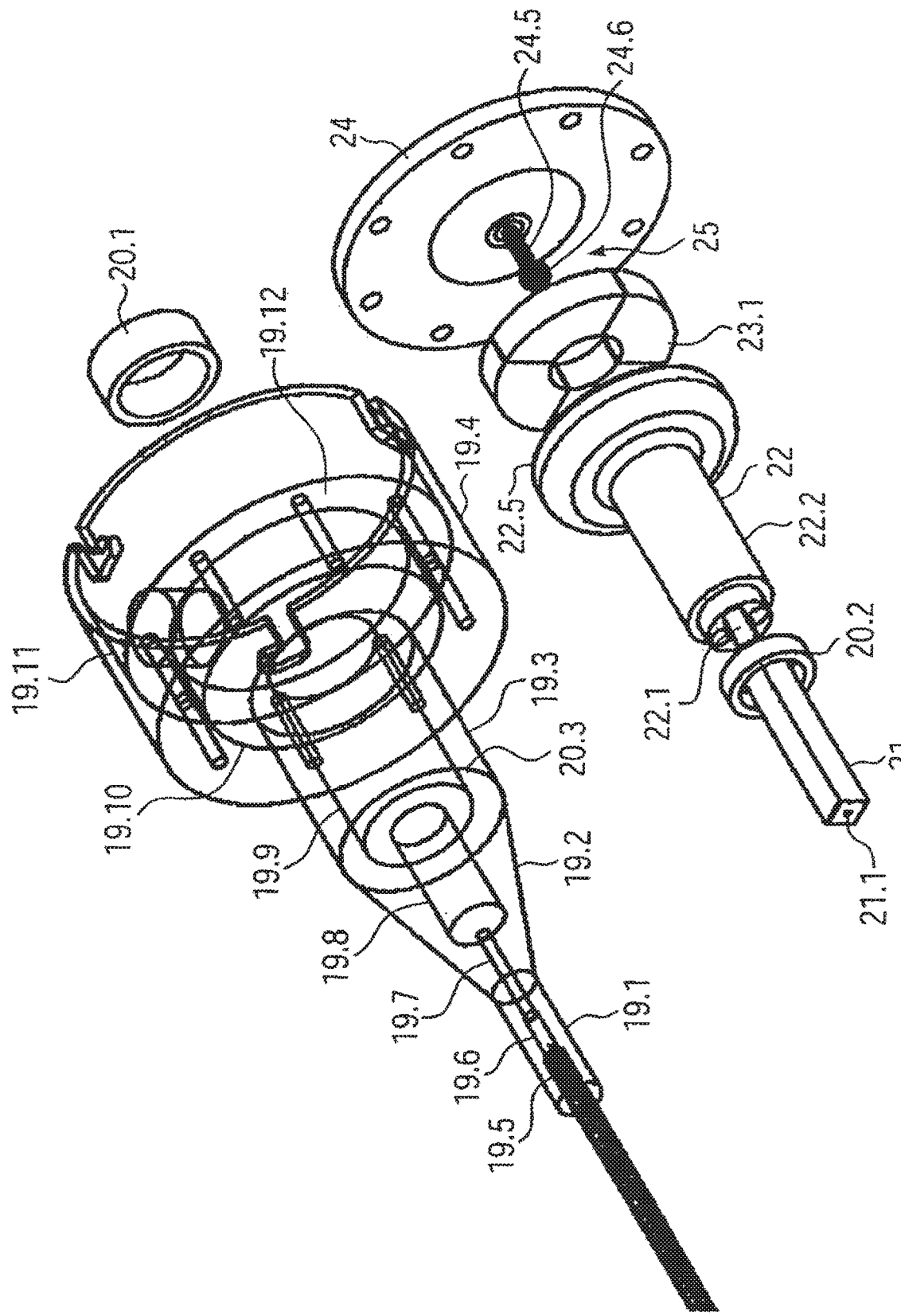

FIG. 15. shows the clutch according to the invention with the clutch housing of the catheter device in a perspective view.

Figure 16:
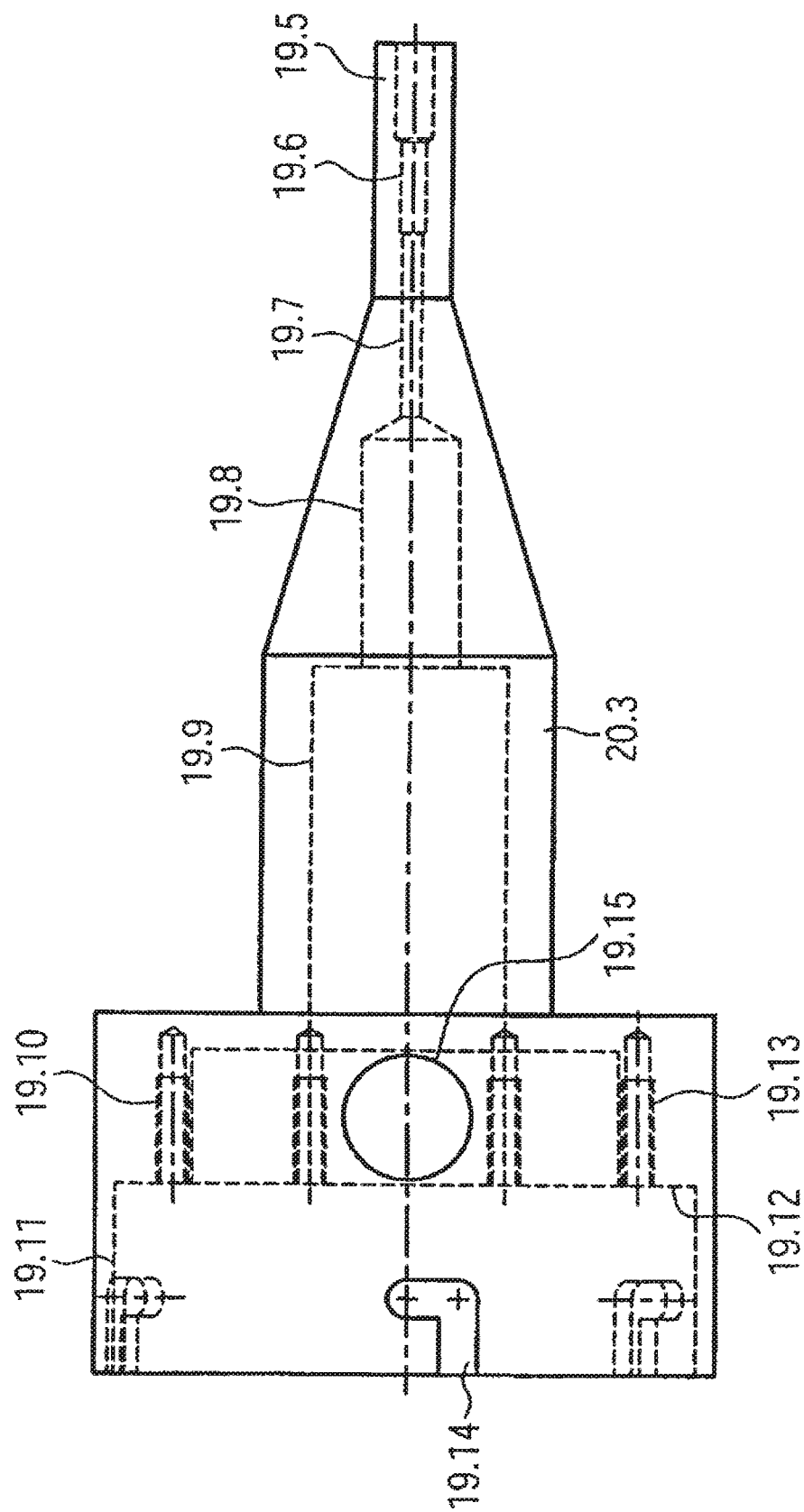

FIG. 16. shows the clutch housing of the catheter device in a perspective view.

Figure 17:
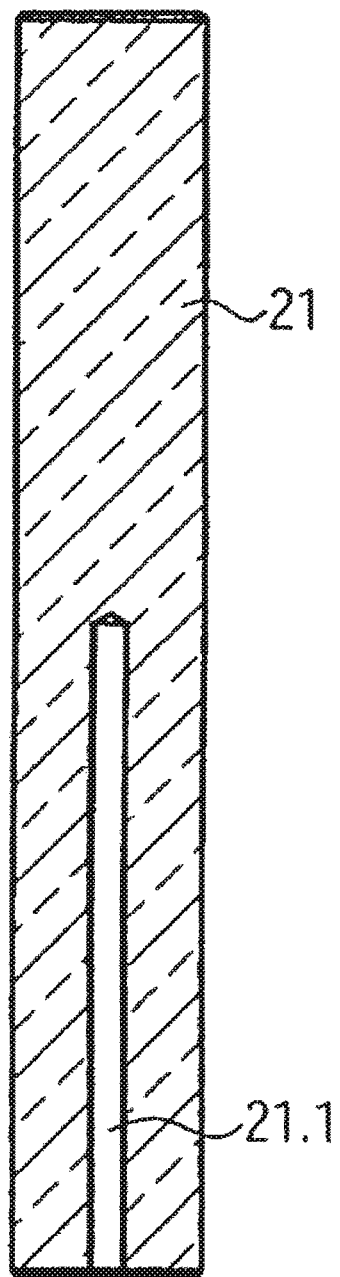

FIG. 17. shows a square rod of the clutch of the catheter device in a side view.

Figure 18:
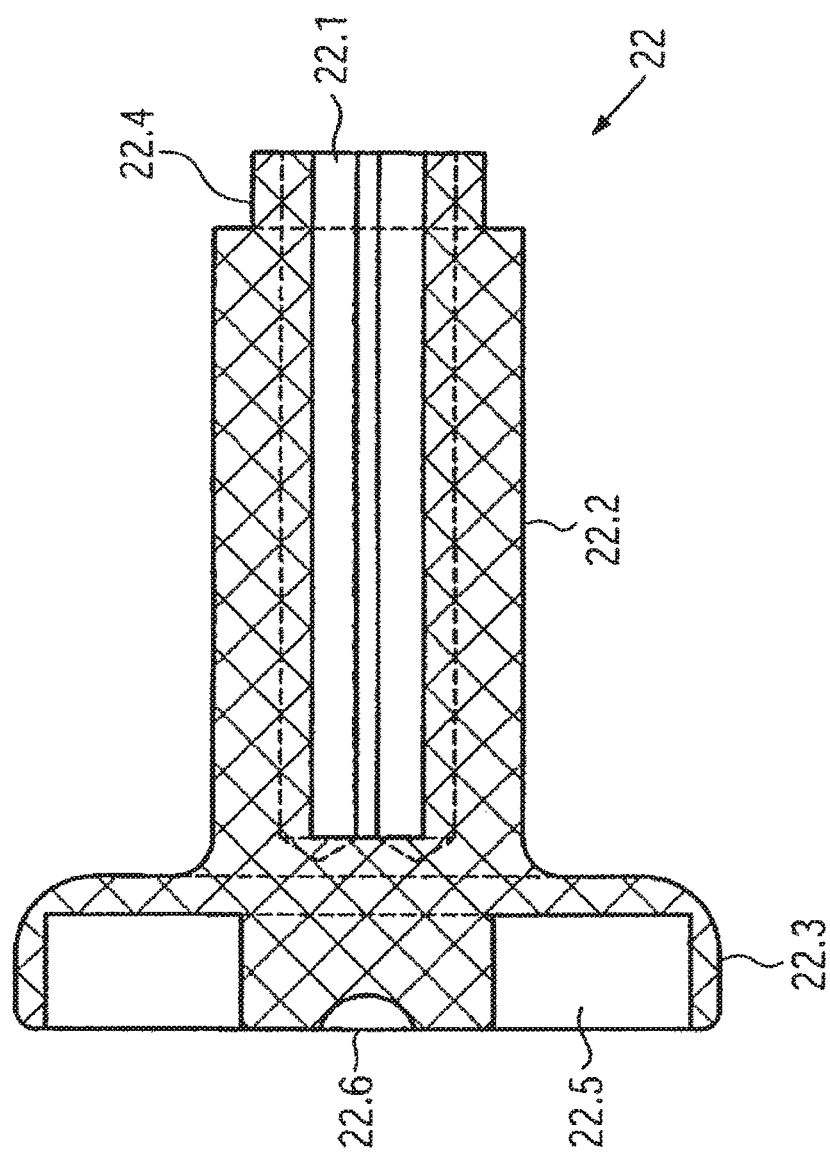

FIG. 18. shows a clutch element of the clutch of the catheter device in a side view.

Figure 19:
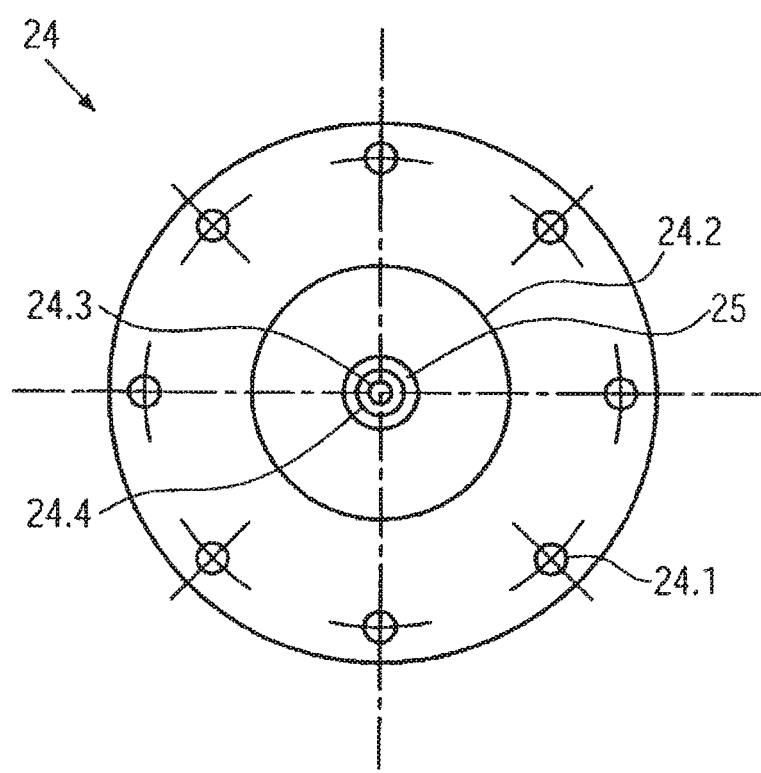

FIG. 19. shows a terminating disc of the clutch of the catheter device in a side view.

Figure 20:
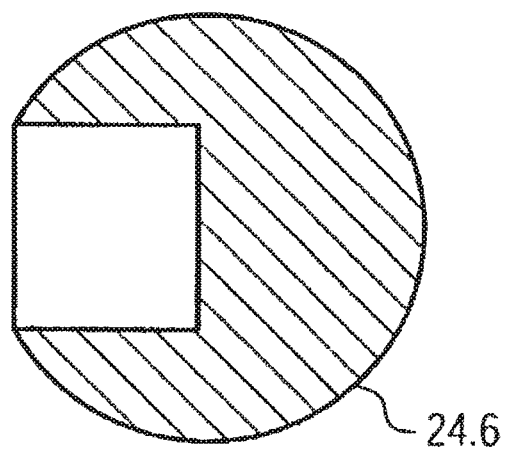

FIG. 20. shows a ball head bearing ball of the clutch of the catheter device in a side view.

Figure 21:
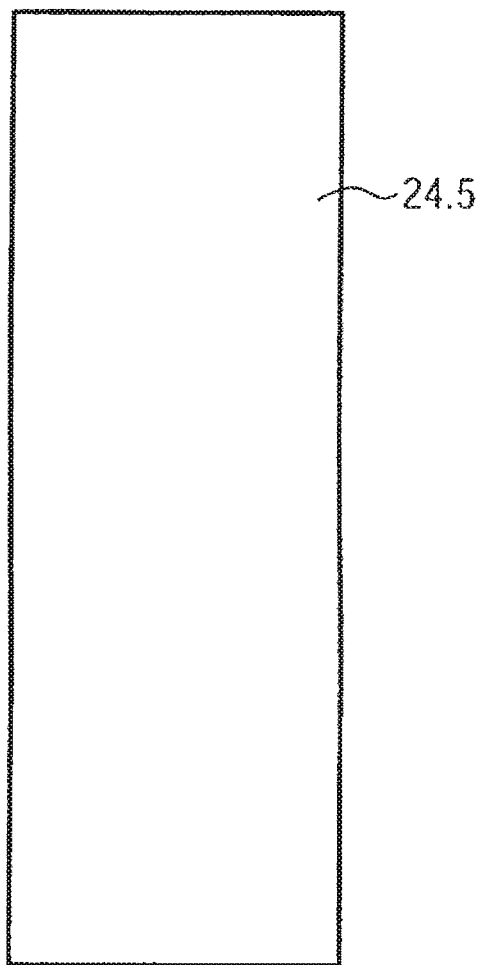

FIG. 21 shows a centering pin of the clutch of the catheter device in a side view.

Figure 22:
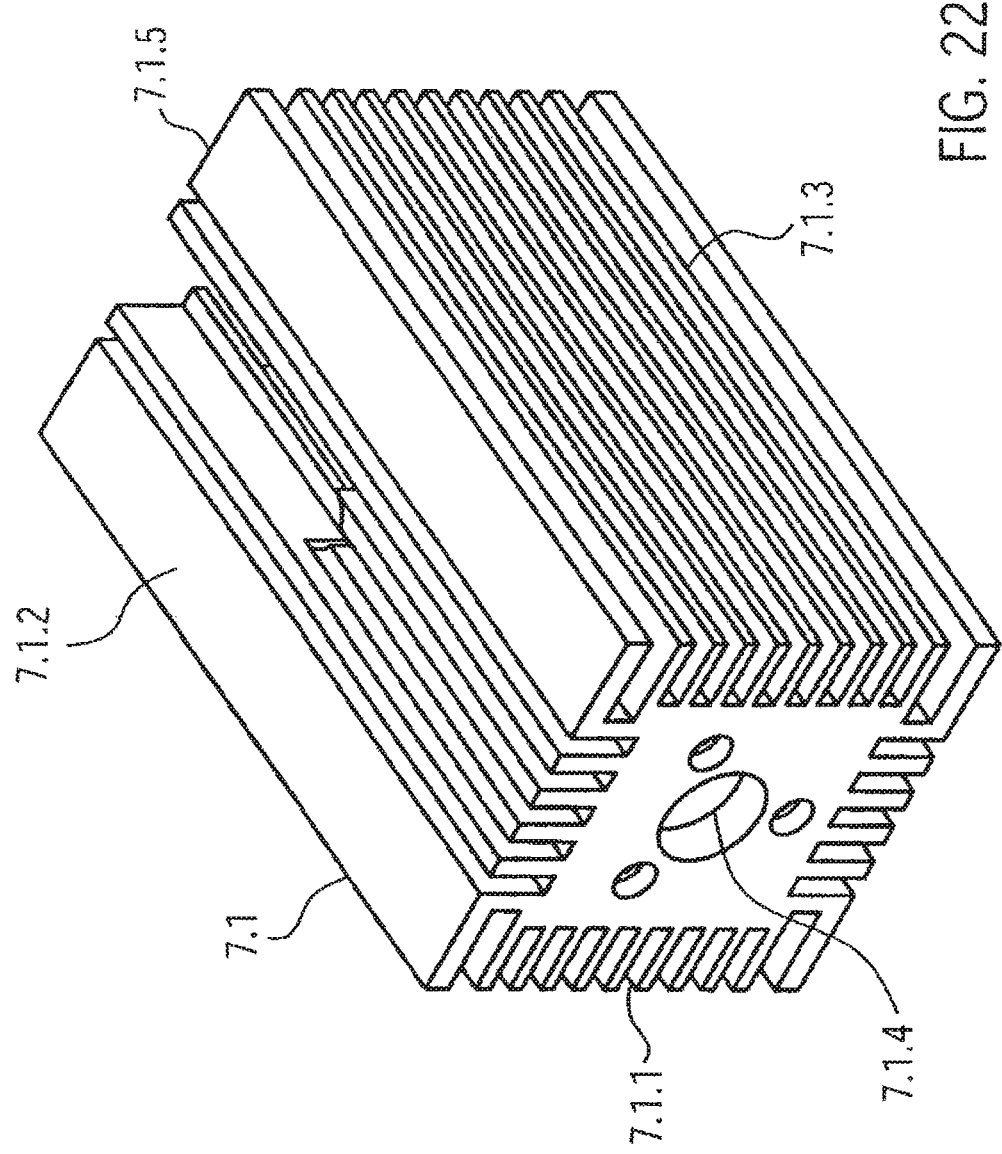

FIG. 22. shows a motor mounting of the catheter device in a side view.

Figure 23:
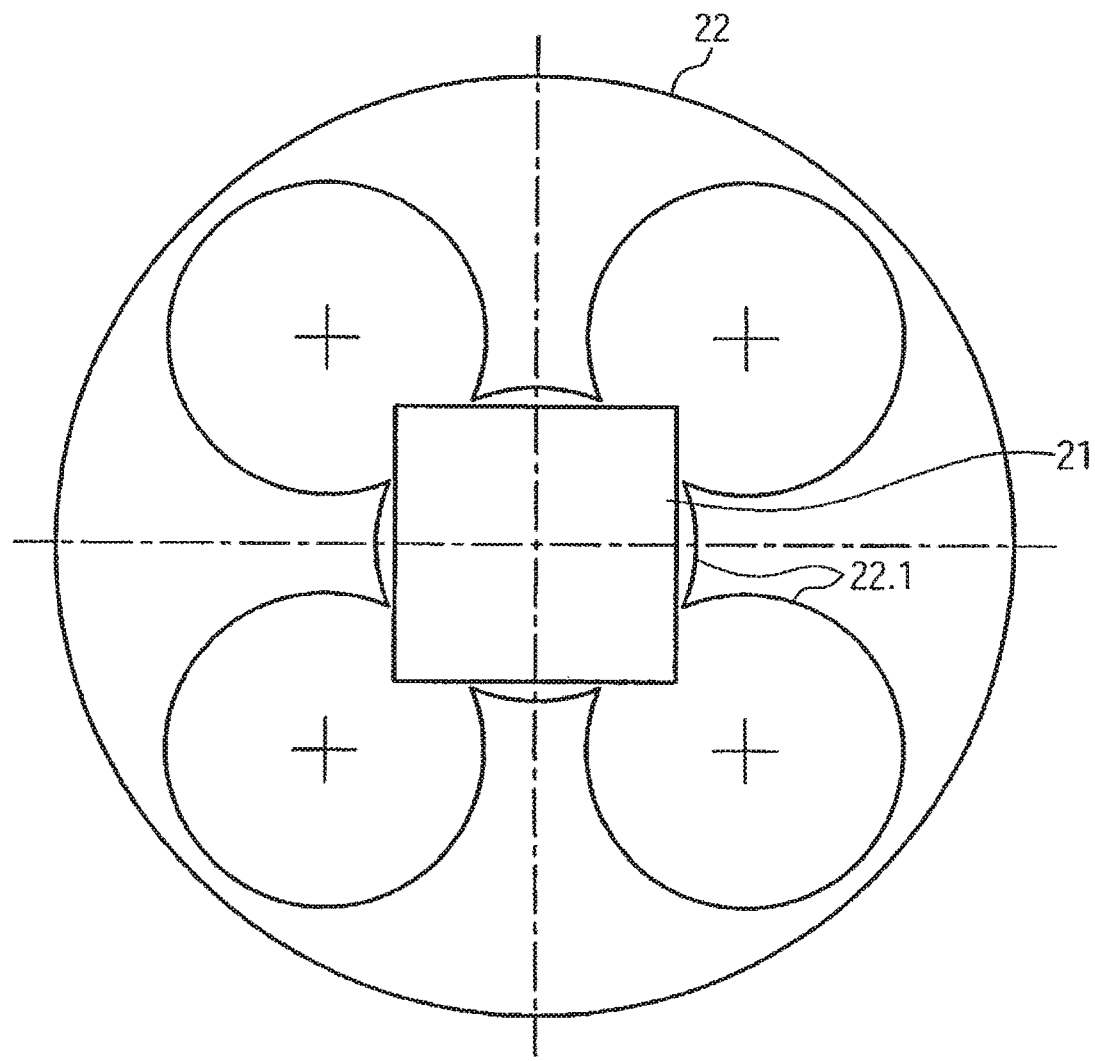

FIG. 23. shows a top view of the clutch element with the square rod contained within it.

Figure 24:
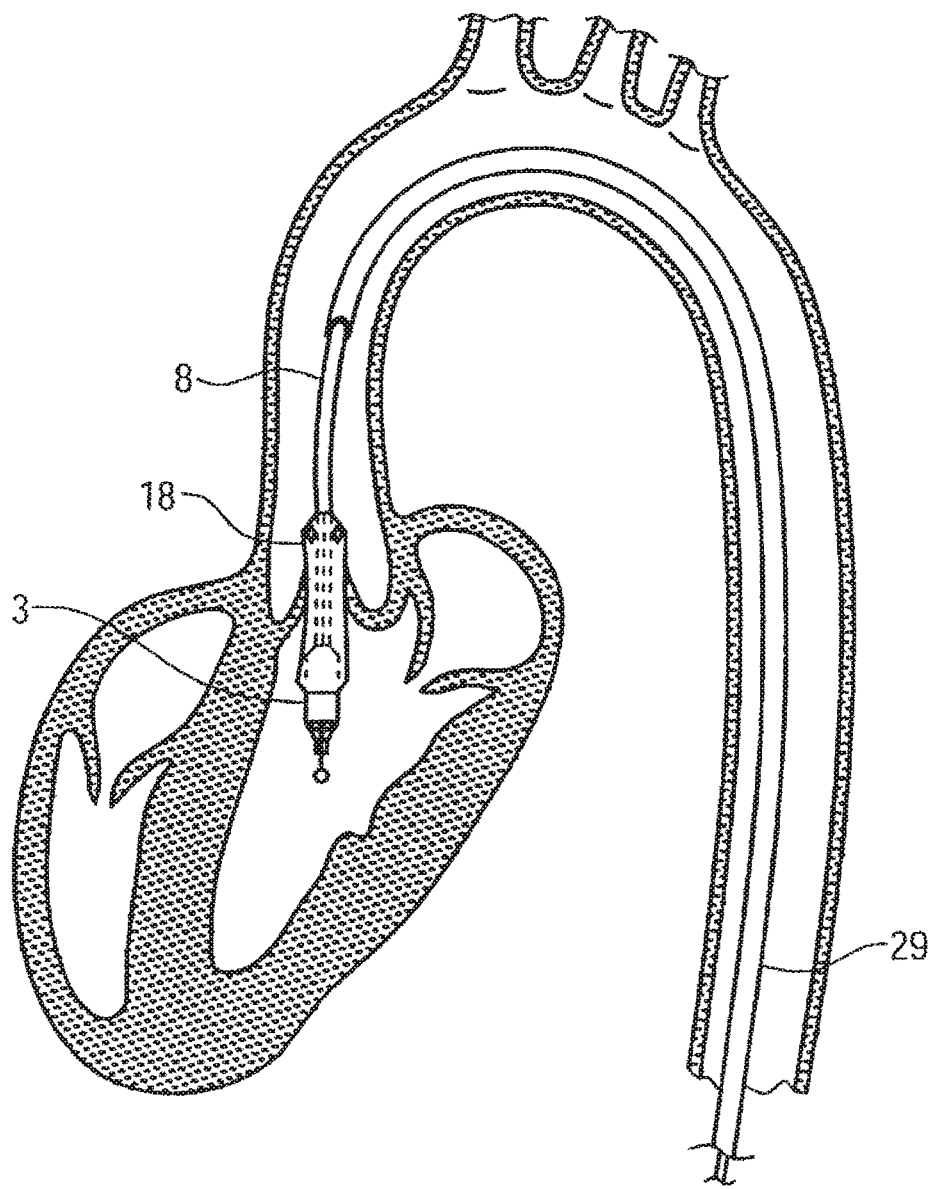

FIG. 24. shows the catheter device positioned in the body.

Figure 25:
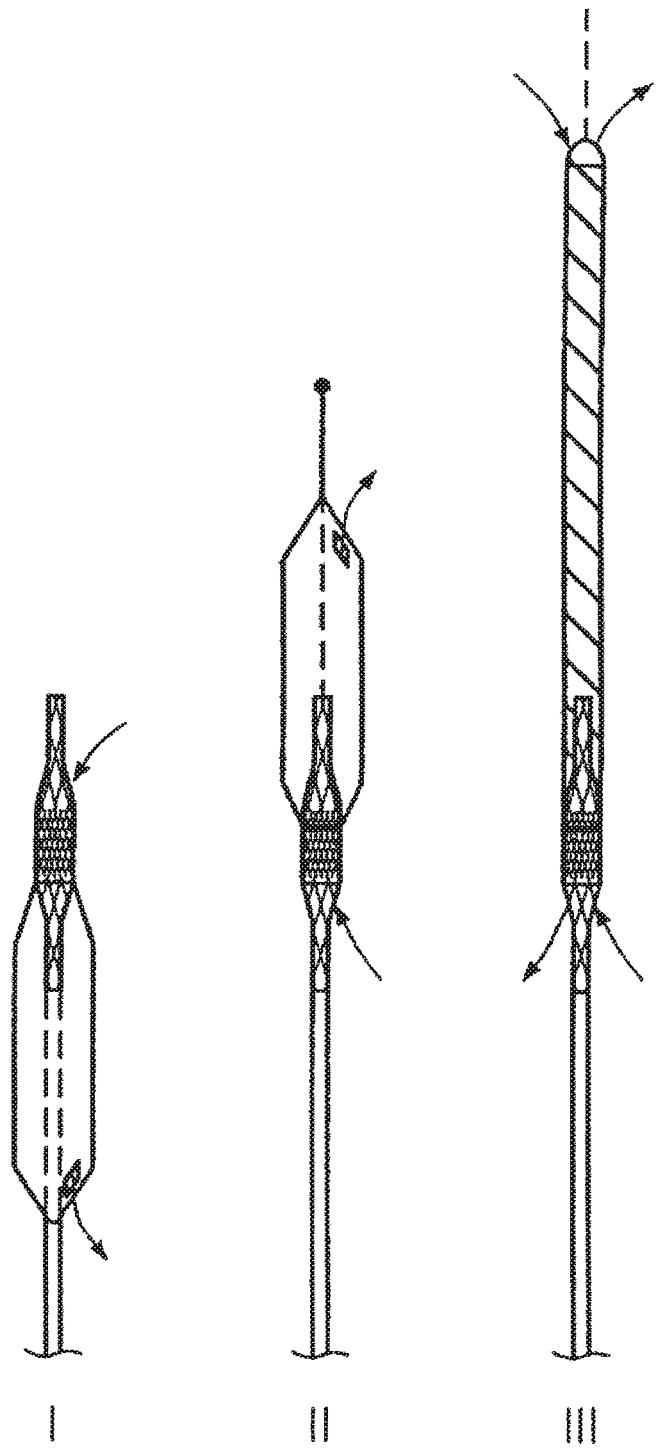

FIG. 25. shows alternative embodiments of the catheter device in schematic form.

DETAILED DESCRIPTION OF THE INVENTION

Figure 1:
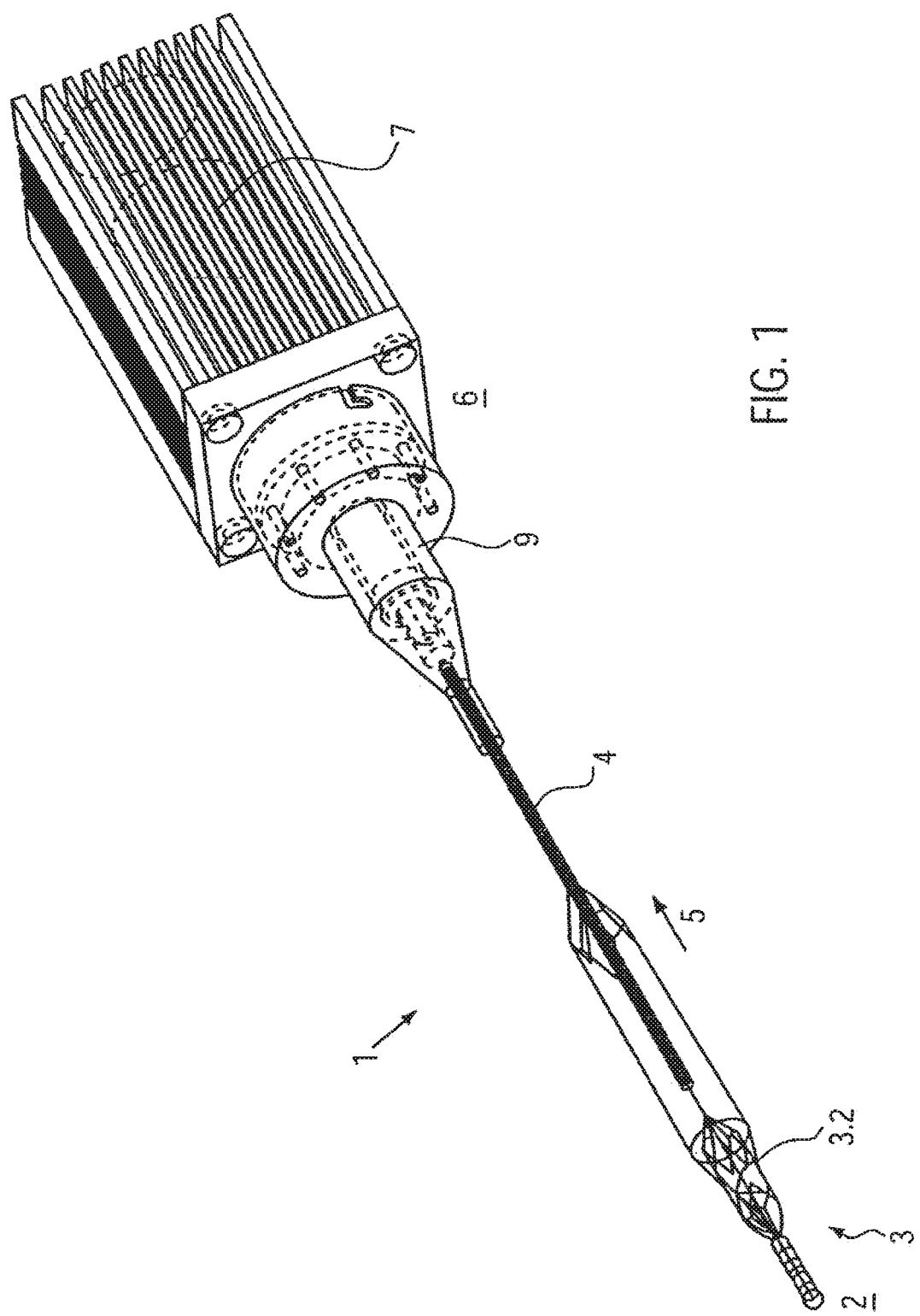

FIG. 1 shows a catheter device 1. The catheter device 1 according to the invention represents a pump. The catheter device 1 has a pump head 3 at a distal end 2.

The pump head 3 has a rotor 3.2, for pumping a medium in the flow direction 5, which is connected to a drive shaft 4. The flow direction 5 is from the distal end 2 to a proximal end 6. Located at the proximal end 6 away from the pump head 3 is a motor 7. The drive shaft 4 is encompassed by a catheter body 8 and connected non-positively by means of a clutch 9 to the motor 7.

First of all the pump head 3 will be explained in more detail below. The pump head 3 comprises a body cap 10 at the distal end, the rotor 3.2 mounted on the drive shaft 4, a pump housing 3.1 and an outlet hose 18.

Figure 2:
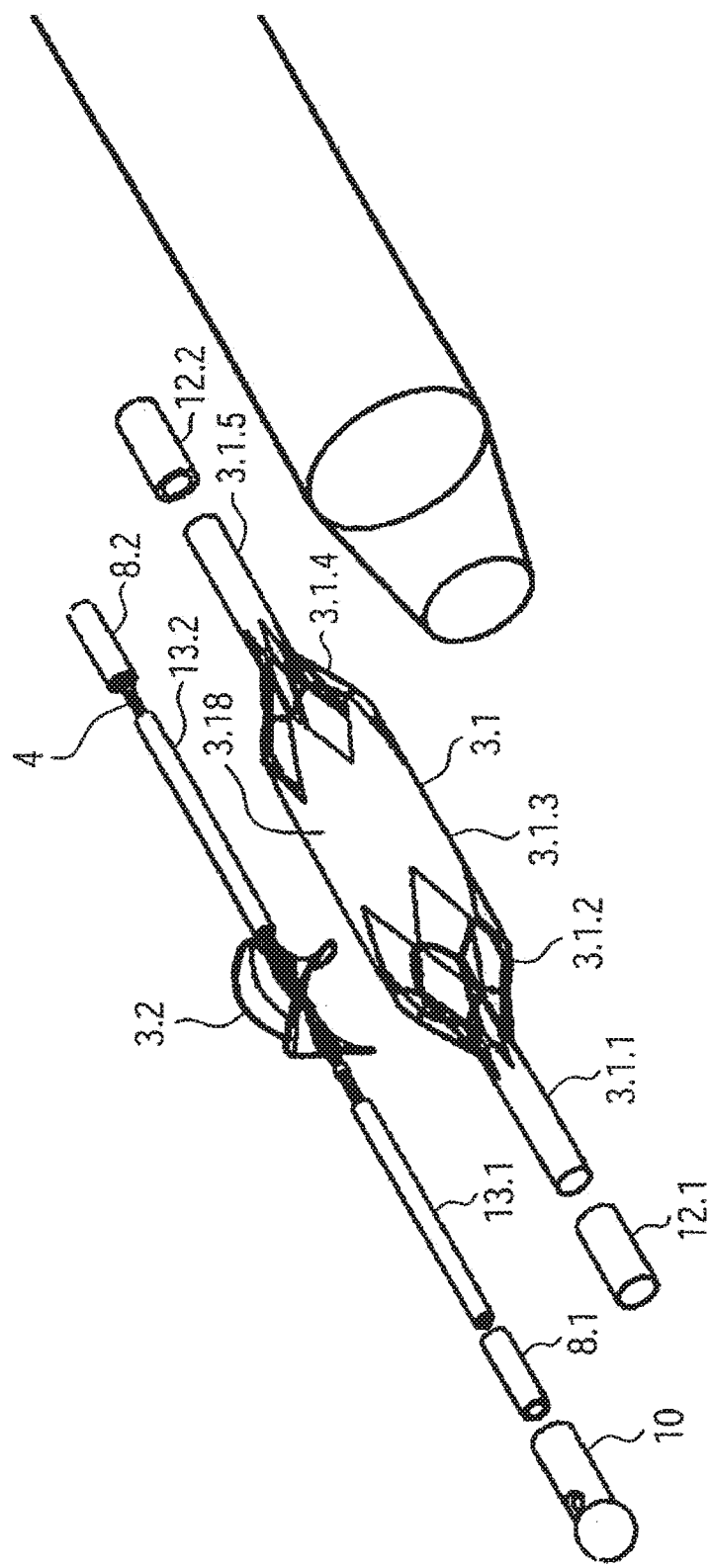
Figure 3:
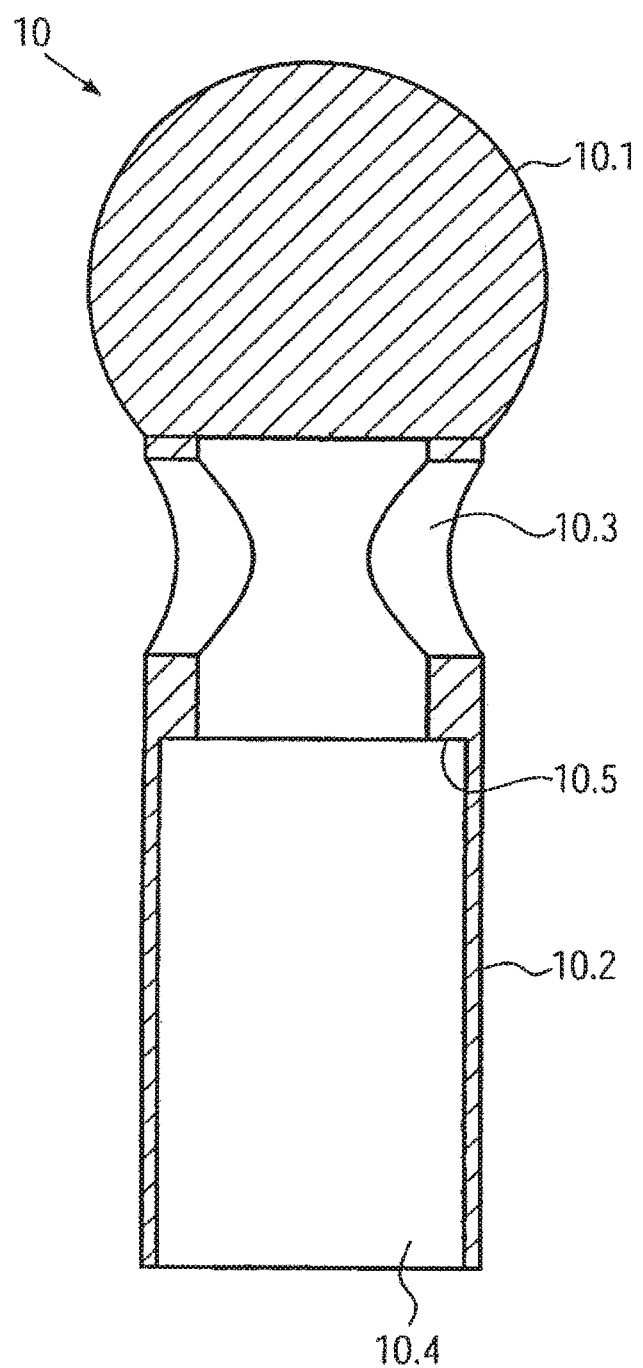

The body cap 10 is formed by a ball 10.1 with an attached cylindrical section 10.2. The body cap 10 is made for example of stainless steel (FIG. 2, FIG. 3). The body cap 10 could be made of polyethylene PE, polypropylene PP, polyether etherketone PEEK, polyvinyl chloride PVC, Teflon PTFE, acrylic glass, epoxy resin, polyurethane PU, carbon fibre, coated materials, composite materials, PEBAX, or a polyether block amide. In principle all haemocompatible materials are suitable, since there is only minimal mechanical loading on this component.

The diameter of the ball 10.1 is roughly 3.2 mm. The cylindrical section 10.2 is around 5.5 mm long and has a diameter of approximately 2.2 mm. The overall length of the body cap is roughly 7.0 mm.

At its distal end, in the area of connection to the ball 10.1, the cylindrical section 10.2 has a through bore 10.3 running at right-angles to the flow direction 5. The cylindrical section 10.2 also has an axial bore 10.4 which extends from the proximal end of the cylindrical section 10.2 to the ball 10.1, thereby forming a communicating passage from the through bore 10.3 to the proximal end of the body cap 10. A step 10.5 is formed in the area of the axial bore 10.4, so that the latter is widened towards the proximal end.

The through bore 10.3 on the one hand avoids the creation of a blind hole in the body cap, while on the other hand permitting the attachment of a thread, which is helpful in compressing the pump head 3.

Instead of the ball 10.1 of the body cap 10, a pigtail, a spiral, a meandering wire with a spherical tip, or an atraumatic fibre bundle may also be provided. The body cap is preferred owing to its small size.

The tip of the body cap 10 is an atraumatic ball to protect the heart muscle (endocardium). Via the body cap 10, the pump head 3 may be supported on the wall of the heart.

Figure 4:
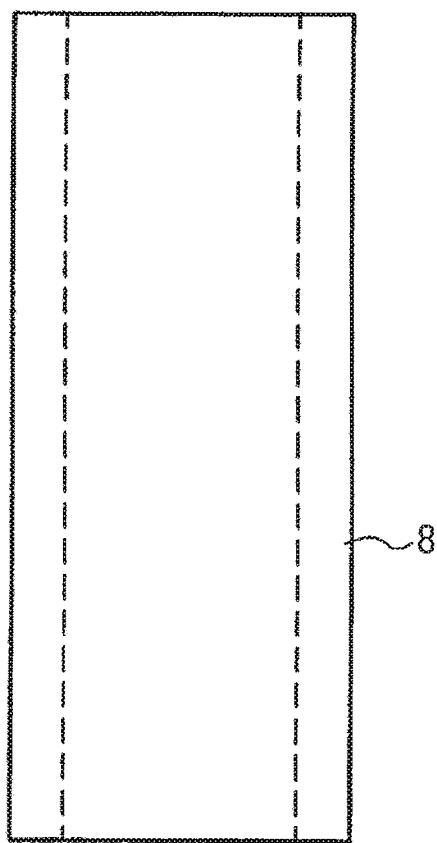

A tubular or hose-like distal catheter body element 8.1 is introduced from the proximal end into the body cap 10 up to the step. The distal catheter body element 8.1 is fixed in the axial bore 10.4 with an accurate fit (FIG. 4). The distal catheter body element 8.1 is made of polyurethane or another suitable material, in particular an elastic, plastic material (e.g. PE, PVC, Teflon, elastomer). The distal end of the distal catheter body element 8.1 is connected to the body cap 10. The connection may be in the form of a bonded joint using for example cyanacrylate adhesive, or may involve a welded, clamped or shrink-on connection. These connection means are suitable in principle for connecting a catheter body element to another, in particular a rigid one. In the description below, therefore, this will not be explained for each individual connection point.

The distal catheter body element 8.1 forms a straight but very flexible connection between the body cap 10 and the pump housing 3.1. The straight connection creates a coaxial alignment of all the parts within it (drive shaft, shaft protector, housing, connection bush).

In combination with the body cap 10, the distal catheter body element 8.1 serves as a positioning aid when the pump head 3 is inserted into a vessel or the heart.

In the present embodiment the catheter body element 8.1 has a length of approximately 25 mm, an outside diameter of around 1.9 mm and an inside diameter of around 1.3 mm.

Figure 5:
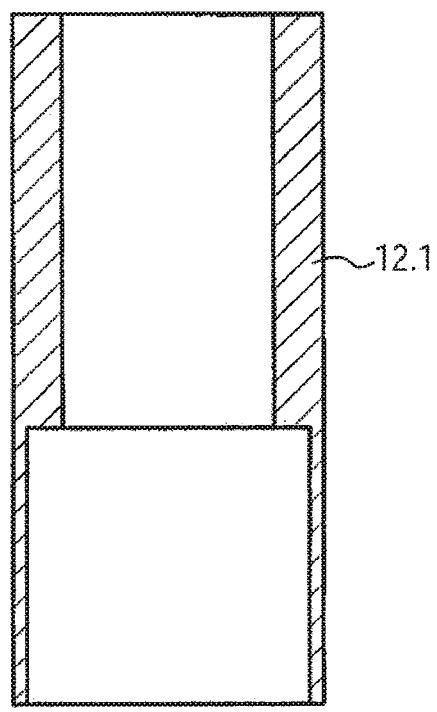
Figure 6:
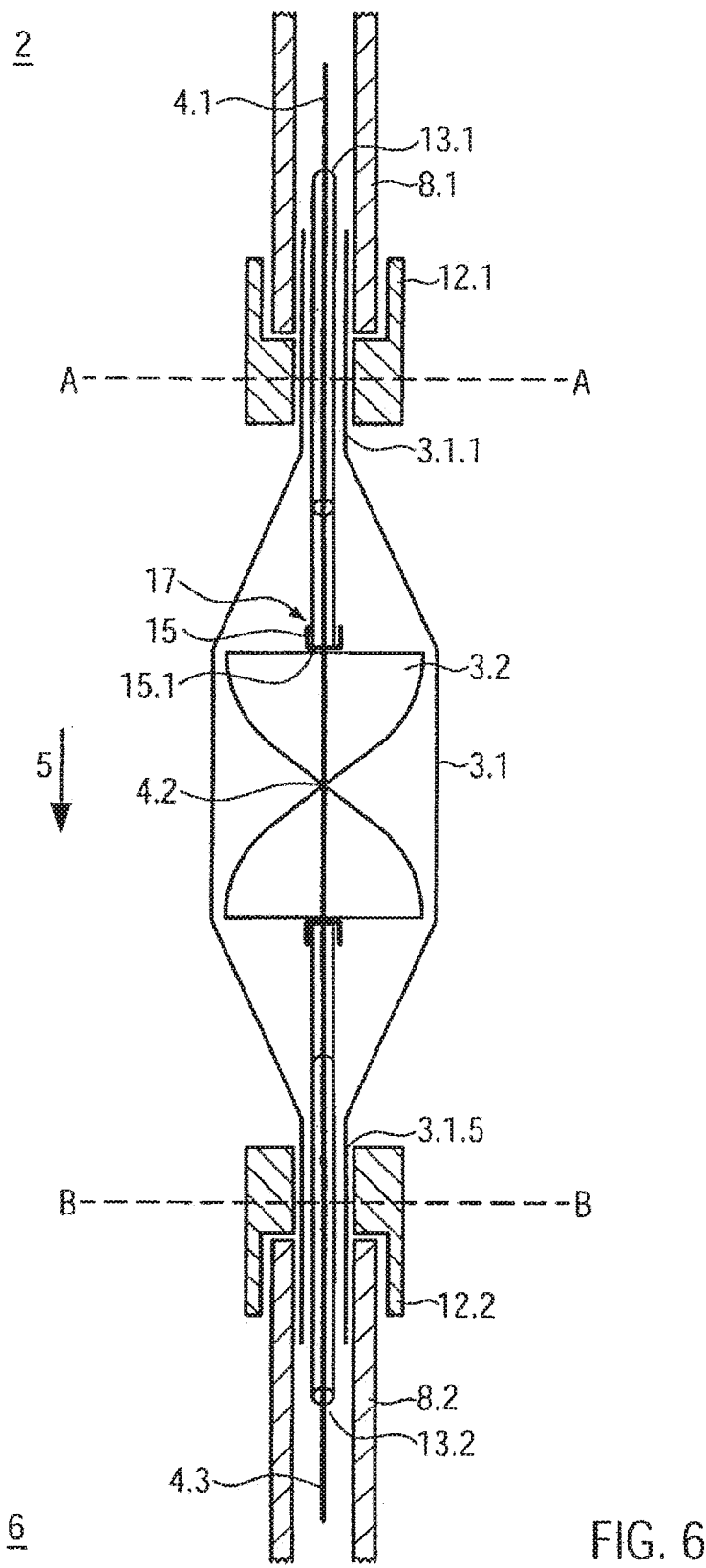
Figure 7A:
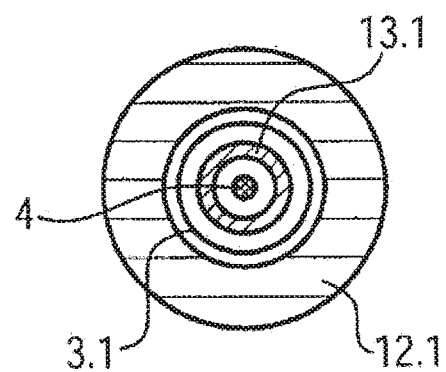
FIG. 7A shows a section along the line A-A through the distal connection bush of the catheter device as shown in FIG. 6.
Figure 7B:
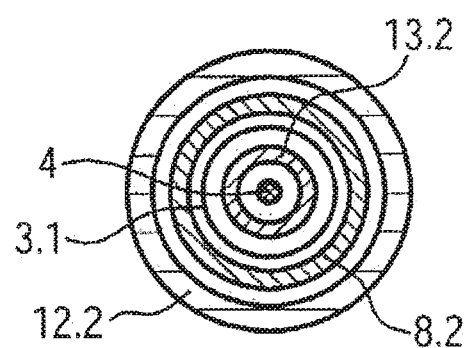
FIG. 7B shows a section along the line B-B through the proximal connection bush of the catheter device of FIG. 6.

Provided at the proximal end of the distal catheter body element 8.1 is a distal tubular connection bush 12.1 (FIG. 5, FIG. 6). The distal connection bush 12.1 has a greater diameter in the distal area than in the proximal area. In the distal area of the connection bush 12.1, the proximal end of the distal catheter body element 8.1 is held with a good fit and fixed in place. Accommodated in the proximal area of the distal connection bush 12.1 is a distal connection section 3.1.1 of the pump housing 3.1. The distal connection section 3.1.1 of the pump housing 3.1 is connected to the distal connection bush 12.1 and the proximal end of the distal catheter body element 8.1 (FIG. 7*a*, FIG. 7*b*).

The distal connection bush 12.1 has a length of around 5 mm and an outside diameter of approximately 2.2 mm. In the distal area, the diameter is roughly 2 mm and in the proximal area it is around 1.5 mm. The shorter the connection bush, the less the reinforcement which it provides.

The distal and a similarly designed proximal connection bush 12.1, 12.2 are made for example of stainless steel, copper, brass, titanium or another suitable metal, of polyethylene (PE), polypropylene (PP), Teflon (PTFE), PEBAX, a polyether block amide or another suitable material.

The expandable or compressible pump housing 3.1 is a tubular mesh structure 3.1.6 of nitinol or another suitable memory alloy or another memory material, e.g. plastic, ferrous alloy, copper alloy. The pump housing 3.1 is divided into five sections from the distal to the proximal end (FIG. 8). The first distal section is a tubular distal connection section 3.1.1. A second section is an intake section 3.1.2 widening conically in the flow direction 5. Next to the intake section 3.1.2 is a pump section 3.1.3. The tubular pump section 3.1.3 holds the rotor 3.2. In the expanded state, the inside diameter of the pump section 3.1.3 is around 6.15 mm. An outlet section 3.1.4 narrows conically in the flow direction 5 and forms the connection between the pump section 3.1.3 and a proximal connection section 3.1.5. The proximal connection section 3.1.5 is, like the distal connection section 3.1.1, tubular with a smaller diameter than the pump section 3.1.3. The pump housing 3.1 may be so compressed that it does not exceed a maximum diameter of less than 3 mm over its whole length.

Between the mesh struts, the mesh structure 3.1.6 of the pump housing 3.1 has apertures 3.1.7 (FIG. 8. FIG. 9). The apertures are in the form of polygons 3.1.7, which in the present embodiment are rhombuses. In the pump section 3.1.3, small rhombuses 3.1.7.1 are provided. In the transition zones from the pump section 3.1.3 to the intake section 3.1.2 and the outlet section 3.1.4 of the tubular mesh structure 3.1.6, the small rhombuses 3.1.7.1 are combined step by step to form increasingly larger rhombuses. Adjacent to a small rhombus is a larger rhombus with twice the edge length. This doubling of edge length is repeated until the apertures reach the desired size. Provided in the intake section 3.1.2 and in the outlet section 3.1.4 are large rhombuses 3.1.7.2 which have roughly four times the edge length of the small rhombuses 3.1.7.1. In the transition zones from the intake section 3.1.2 and the outlet section 3.1.4 to the distal and proximal connection sections 3.1.1, 3.1.5 of the tubular mesh structure 3.1.6, the large rhombuses 3.1.7.2 are turned into smaller rhombuses. In the distal and proximal connection sections, medium-sized rhombuses 3.1.7.3 are provided which have approximately double the edge length of the small rhombuses 3.1.7.1 (FIG. 9). The layout of the apertures 3.1.7 and the number of increases in size may be as desired. In the transition from smaller to larger rhombuses the width of the mesh struts is increased. In this way the strength of the mesh struts is kept roughly the same, and even increased towards the larger rhombuses.

The mesh structure 3.1.6 of the pump housing 3.1 is covered in the pump section 3.1.3 by a PU covering 3.1.8, which provides a liquid-proof seal of the mesh apertures.

This covering and the sealing of the mesh structure 3.1.6 may also be provided by a PU hose fitted on to the outer or inner surface.

Other coverings than PU may also be used, e.g. PE, PP, silicone or parylene, so long as the mechanical and geometrical requirements are met.

Through the selection of individual apertures 3.1.7.1, in particular the medium- and larger-sized apertures 3.1.7.3, 3.1.7.2, which are not coated, the performance parameters including blood damage from the pump, may be controlled in a targeted manner.

The polygonal structure and the special finish of the PU covering result in the pump housing 3.1 having an approximately round cross-section. In combination with the round rotor 3.2, this leads to very small gaps between the rotor 3.2 and pump housing 3.1. This leads to comparatively low blood damage, low leakage rates and high efficiency. The mesh structure 3.1.6 provides very good radial and axial stability together with very good axial compression and expansion properties. The special structure makes possible very easy adaptation of length and diameter to performance requirements.

The proximal connection section 3.1.5 of the pump housing 3.1 is held in and connected to the proximal connection bush 12.2. In the proximal connection bush 12.2, as in the distal connection bush 12.1, a hose-like proximal catheter body piece 8.2 is located and connected to it (FIG. 7a, FIG. 7b). The same types of connection as already described above may be provided.

Arranged axially within the distal and the proximal catheter body element 8.1, 8.2 are a distal shaft protector 13.1 and a proximal shaft protector 13.2 (FIG. 6). The distal and proximal shaft protectors 13.1, 13.2 are in the form of hose made of PU or one of the other materials already referred to above.

The distal shaft protector 13.1 extends in the flow direction 5 from shortly before the distal connection bush 12.1 to the distal end of the pump section 3.1.3 of the pump housing 3.1, i.e. as far as the rotor 3.2. The proximal shaft protector 13.2 extends from the proximal end of the rotor 3.2 until shortly after the proximal end of the distal connection bush 12.1.

In the two areas in which they lie within the distal and the proximal connection bushes 12.1, 12.2 and the distal and proximal catheter body elements 8.1, 8.2 respectively, the distal and proximal shaft protectors 13.1, 13.2 are joined to these former components.

Together with the components mounted within them (shaft protector, pump housing, catheter body), the two connection bushes 12.1, 12.2 form a bearing section for the drive shaft 4. The connection bushes 12.1, 12.2 ensure the axial centricity of the drive shaft 4 in particular in the pump housing 3.1.

The drive shaft 4 is mount axially within the distal and proximal shaft protectors 13.1, 13.2 and the pump housing 3.1 respectively. In the flow direction 5 the drive shaft 4 has three sections: a distal section of the drive shaft 4.1 in the area of the body cap 10; a pump section of the drive shaft 4.2 on which the rotor 3.2 is non-rotatably mounted; and a proximal section of the drive shaft 4.3 extending from the pump section 3.1.3 to the clutch 9. The rotor 3.2 is adhesive-bonded to the drive shaft. Other non-positive types of connection such as welding or clamping may however also be provided.

To guard against blood damage due to the rotation movement of the drive shaft 4 and adhesion of blood constituents to the drive shaft 4, the proximal shaft protector 13.1 (FIG. 2, FIG. 6) separates the proximal section 4.3 of the drive shaft 4 physically from the pump medium. This prevents the build-up of shear forces. There is no direct interaction between the drive shaft 4 and the blood due to the very small gap, and only minimal transport of blood through this gap is possible. The distal and proximal shaft protectors 13.1, 13.2 centre and support the drive shaft 4 in operation and during the compression and expansion process.

The drive shaft 4 is preferably formed by several, in particular six, wires (not shown) wound to left or right around a core. The outside diameter of the drive shaft 4 is roughly 0.48 mm. The drive shaft 4 may however also have a different number of cores and wires and a smaller or larger diameter. The diameter of the drive shaft may lie in the range between 0.3 mm and 1 mm, and is preferably around 0.4 mm to 0.6 mm. The smaller the diameter of the drive shaft, the greater the possible speed, since the smaller the diameter the greater is the speed at which the periphery of the drive shaft moves relative to its environment. A high peripheral speed is problematic when the drive shaft comes into contact with the environment. The catheter device is designed for speeds of more than 20,000 rpm and up to 40,000 rpm. The diameter of the drive shaft 4 is therefore made as small as possible, but thick enough to give it adequate strength.

Against the direction of winding of the drive shaft 4—in the present embodiment it is wound to the left—is a guide spiral 14 with opposite winding (here wound to the right) fitted axially around the distal and proximal sections of the drive shaft 4.1, 4.3. Its purpose is to minimise friction of the drive shaft 4, to avoid wall contact of the drive shaft 4 with the proximal catheter body element 8.2, and to prevent kinking of the drive shaft 4 as a result of bending. Through the guide spiral 14, the drive shaft 4 is guided and fixed or stabilised (FIG. 10). The guide spiral 14 may be made of stainless steel and glued to the shaft protector 13.1, 13.2. The guide spiral may also be provided in the form of a spring. The direction of winding of the guide spiral 14 may also be the same as the direction of winding of the drive shaft 4.

The drive shaft 4 extends from the distal end of the distal shaft protector 13.1 in the flow direction 5 behind the distal connection bush 12.1 to the clutch 9.

In combination with the guide spiral 14, the proximal catheter body element 8.2 provides a connection, constant in length and torsion, between the pump head 3 and the clutch 9.

Provided at the proximal end of the distal shaft protector 13.1 is a bearing washer 15 (FIG. 6). The bearing washer 15 is provided with a through bore 15.1. The diameter of the through bore 15.1 corresponds roughly to the outside diameter of the drive shaft 4. The bearing washer 15 is fitted on to the drive shaft 4 in such a way that it holds the proximal end of the distal shaft protector 13.1, bounding it in the flow direction 5.

The bearing washer 15 is made for example of stainless steel, Teflon or a ceramic or other suitable material. The bearing washer 15 is bonded to the stationary shaft protector using cyanacrylate adhesive and is therefore able to absorb axial forces against the flow direction 5 (for means of connection see above).

In the pump section 4.2 of the drive shaft 4, the spiral-shaped, expendable rotor 3.2 is mounted non-rotatably on the drive shaft 4. Provided as rotor 3.2 in the present embodiment is a two-blade, comb-shaped frame structure 3.2.1 of nitinol or another memory material, e.g. plastic (see above), which is coated or encompassed with fluid-tightness by a PU skin (FIG. 11a). I.e. the covering in the form of the PU skin is stretched between the comb-like frame structure. Because of the structure of the rotor 3.2 as a coated frame structure 3.2.1 of nitinol, it is possible to expand or compress the rotor 3.2. The PU skin has high elasticity so that it is not damaged during compression.

The frame structure 3.2.1 has a continuous screw-like or spiral-shaped outer boundary frame 3.2.2 with several rotor struts 3.2.3 connected to the boundary frame 3.2.2 and running radially inwards (FIG. 12). Rings 3.2.4 are formed at the free ends of the rotor struts 3.2.3. The drive shaft 4 extends through the rings 3.2.4 of the rotor struts 3.2.3.

Provided between every two adjacent rings 3.2.4 there is a spacer sleeve 16. The distal end of the rotor 3.2 abuts the bearing washer 15 with a distal-end spacer sleeve 16. The end spacer sleeves 16 may also be in the form of a special bearing spacer sleeve 16. In this way two of the frame structures 3.2.1 form a two-blade rotor 3.2.

The rotor 3.2 may also be made in one piece (FIG. 11b) or have several frame structures (FIG. 11a). Each frame structure forms a rotor blade. FIGS. 11b and 12 show a frame structure 3.2.1 for a rotor 3.2 which forms two rotor blades. If required, it is also possible for several rotor blades and therefore several frame structures 3.2.1 to be fitted to a rotor 3.2. The frame structure may also take any other suitable form.

The distance between two adjacent rings 3.2.4 is less than the corresponding section of the spiral-shaped boundary frame 3.2.2. The greater the difference between the distance between two rings 3.2.4 and the corresponding section of the spiral-shaped boundary frame 3.2.2, the greater the pitch of the rotor. The pitch of the rotor 3.2 may thus be set by the length of the spacer sleeves 16, and may be varied within a rotor 3.2.

The pitch of the rotor 3.2 is determined by the length and number of spacer sleeves 16 relative to the dimensioning of the continuous spiral-shaped outer boundary frame 3.2.2 between two rotor struts 3.2.3. The length of the spacer sleeves 16 may be standard for all positions, but may also be varied symmetrically or asymmetrically for each position. The complete freedom for configuration makes possible very flexible design of the rotor 3.2, in turn permitting different pump properties for the rotor 3.2.

The rotor 3.2 has high dimensional stability combined with flexible scope for configuration with minimum use of material (e.g. thin frame structure). Maximum stiffness and stability are obtained. Nevertheless the combination of the frame structure and the covering, which further supports the properties of the frame structure through stabilisation, allows very strong compression. This leads to very good compressibility and expandability of the rotor. Owing to the good surface formation of the PU skin on the mesh structure, very good matching of the housing structure to the rotor structure is possible.

In the compressed state, the rotor 3.2 has approximately the inside diameter of the compressed pump housing 3.1. The outside diameter of the compressed pump housing is roughly between 2 mm and 4 mm and preferably around 3.3 mm.

In the expanded state, the spiral-shaped outer boundary frame 3.2.2 of the rotor 3.2 is a very short distance away from the inner surface of the pump housing 3.1. The distance between the outer boundary frame 3.2.2 and the inner surface of the pump housing 3.1 is roughly between 0.01 mm and 0.5 mm. The smaller the distance between the frame structure 3.2.1 and the inner surface of the pump housing 3.1, the greater the pump performance of the rotor 3.2.

At the distal-end spacer sleeve 16 of the rotor there is contact with the bearing washer 15 fixed to the distal shaft protector 13.1 and the distal-end spacer sleeve 16, both of which are fitted on to the drive shaft 4. Since the rotor 3.2 is set into a rotary motion by the drive shaft 4, the distal spacer sleeve 16 of the rotor 3.2 contacts the bearing washer 15 in the manner of a sliding bearing. In this way a distal rotor bearing 17 is formed (FIG. 6). The drive shaft 4 is held almost free from play by the through bore of the bearing washer 15. Only small free spaces (not shown) remain, however, due to the design of the drive shaft 4.

During positioning, on account of the flow of the pump medium, the rotor 3.2 is loaded with an axial force against the flow direction 5. This force is diverted via the distal-end spacer sleeve 16 on to the bearing washer 15.

To lubricate the distal rotor bearing, blood or serum is sucked in via the through bore 10.3 of the body cap 10, the open spaces between the distal shaft protector 13.1 and the drive shaft 4, and the open space between the drive shaft and the bearing washer 15. The suction effect occurs due to the rotary movement of the drive shaft 4 and the rotor 3.2.

At the proximal-end spacer sleeve 16 of the rotor 3.2, the drive shaft 4 is similarly held by a proximal connection bush 12.2.

Located at roughly the proximal end of the pump section 3.1.3 of the pump housing is a tubular elastic outlet hose 18 (FIG. 1, FIG. 13). The outlet hose 18 is made of PU and has a length of approximately 70 mm, a diameter of around 10 mm and a wall thickness of roughly 0.01 mm to 0.1 mm and preferably around 0.03 mm. The two ends of the outlet hose 18 are tapered, with a cylindrical section being provided at the proximal conical end of the outlet hose.

The distal tapering end of the outlet hose 18 makes a tight seal with the PU covering of the pump section 3.1.3 of the pump housing 3.1. The cylindrical proximal section is connected securely to the proximal catheter body element 8.2. Both are joined together with a fluid-tight seal by means of dissolved PU.

Located at the proximal end of the outlet hose 18 are several radially consecutive outlets 18.1. The outlets 18.1 may be oval in the flow direction 5. It is however also possible to make the outlets circular, half-moon-shaped or with any other geometry in order to generate different outflows. The outlets 18.1 agitate the blood passing out into the aortic bulb. This prevents a laminar flow with a resultant water jet pumping effect on the coronary arteries.

The outlet hose 18 takes the pump volume of the pump from the left ventricle via the aortic valve into the aorta. Here the outlet hose 18 acts like a non-return valve. If there is a positive pressure difference between the outlet hose 18 and the aorta, then the outlet hose 18 is open to a greater or a lesser extent depending on the flow volume generated by the pump. With a nil or negative pressure difference, the outlet hose 18 closes just like the aortic valve due to its high flexibility, and lies closely against the proximal catheter body element 8.2. This flexibility leads to good sealing during through flow, against the vela of the aortic valve. Because of this, there is only minimal backflow from the aorta into the left ventricle.

Located at the proximal end of the catheter body element 8.2 are the clutch 9 and the motor 7. The distance between the pump head 3 and the clutch 9 and the length of the proximal catheter body element 8.2 respectively may vary according to the patient and are approximately 90 to 150 cm.

The method of expanding the rotor 3.2 is described below.

Fitted over the catheter device 1 is a tubular cover hose 29, so designed as to encompass the compressed pump head 3 together with the proximal catheter body element 8.2. The cover hose 29 holds the pump head 3 in its compressed state.

After the pump head 3 has been correctly positioned, the cover hose 29 is withdrawn from the fixed catheter device 1 until the pump head 3 is free. Due to the spring force of the elastic material, the pump housing 3.1 and the rotor 3.2 unfold radially outwards. In other words, the mesh structure 3.1.6 of the pump housing 3.1 and the frame structure 3.2.1 of the rotor 3.2 expand until they have reached their preset diameter. Temperature effects of the memory material may also be utilised to assist in the expansion process.

To remove the catheter device 1, the cover hose 29 is pushed forward up to the body cap 10, causing the rotor 3.2 and the pump housing 3.1 to be compressed and drawn into the cover hose, after which the latter is extracted through the puncture point.

The clutch 9 and the motor 7 are explained below.

The clutch 9 is a magnetic clutch (FIG. 14, FIG. 15). The clutch 9 has a clutch housing 19 with a distal magnet unit 23.1. The clutch housing 19 is connected to the proximal catheter body element 8.2, which forms a continuous hollow space. The clutch housing 19 separates the proximal catheter body element 8.2 hermetically from a motor assembly 30. The motor assembly 30 has a proximal magnet unit 23.2. The proximal magnet unit 23.2 is connected non-positively to the motor 7. The distal magnet unit 23.1 is connected to the drive shaft 4 via a clutch element 22.

The distal magnet unit 23.1 and the proximal magnet unit 23.2 are coupled non-rotatably to one another through magnetic forces. A non-positive connection with non-contact rotational force transfer is ensured by the two magnet units 23.1, 23.2.

From the distal to the proximal end, the clutch housing 19 has a distal cylindrical section 19.1, a conically expanding section 19.2, a second cylindrical section 19.3 and a proximal cylindrical section 19.4. The clutch housing is made e.g. of polymethylacrylate (PMMA) or another material which can be injection-moulded or machined.

Formed in the distal cylindrical section 19.1 is a through bore, positioned centrally in the axial direction. The through bore extends through the whole of the clutch housing 19.

From the distal end of the distal cylindrical section 19.1, the through bore narrows in three stages from a first catheter body mounting section 19.5 to a second guide spiral mounting section 19.6 and to a third drive shaft passage section 19.7.

The bore diameter of the catheter body mounting section 19.5 is around 1.9 mm, that of the guide spiral mounting section 19.6 approximately 1.28 mm and that of the third bore section roughly 1.0 mm.

The proximal end of the proximal catheter body is located in and securely connected to the catheter body mounting section 19.5 of the clutch housing 19. The guide spiral 14 is mounted in the guide spiral mounting section 19.6.

The drive shaft 4 extends through the through bore of the drive shaft passage section 19.7 of the distal cylindrical section 19.1 and of the conically widening section 19.1, 19.2. The drive shaft passage section 19.7 widens in the conically widening section 19.2 into a fourth bore section 19.8.

At the start of the second cylindrical section 19.3, the fourth bore section merges into a hollow-cylindrical bearing section 19.9. Located in the distal end section of the bearing section 19.9 is an outer ring magnet 20.1. The outer ring magnet 20.1 is fixed in the bore of the bearing section 19.9 by a press fit, and may also or alternatively be fixed by adhesive bonding.

The bearing section 19.9 has a diameter of approximately 10 mm.

At the start of the proximal cylindrical section 19.4 of the clutch housing 19, the bore of the bearing section 19.9 merges into a larger sixth distal clutch section 19.10. Formed in the distal clutch section 19.10 is a radially aligned rinsing bore 19.15.

Connected to the rinsing bore is a pump (not shown) for the introduction of a medium (e.g. NaCl, glucose solution, Ringer's solution, plasma expander, etc.).

The bore of the distal clutch section 19.10 merges into a larger proximal clutch section 19.11. Formed in the shoulder 19.12 between the distal and proximal clutch sections 19.10, 19.11 are radially symmetrical 8×M 1.6 tapped holes 19.13. At the proximal end of the proximal section 19.4, three L-shaped recesses 19.14 are distributed around the periphery.

The distal clutch section 19.10 has a diameter of approximately 22 mm. The rinsing bore 19.15 has a diameter of around 6.5 mm and the proximal clutch section 19.11 has a diameter of around 30 mm.

The proximal end of the drive shaft 4 is connected non-rotatably and secure against tension and compression (non-positively) to a square rod 21 (FIG. 17). In the axial direction the square rod 21 has a recess 21.1 to accommodate the proximal end of the drive shaft 4. The drive shaft 4 is fixed in the recess. The square rod 21 is made e.g. of brass, which has good lubrication properties. Other suitable materials are all those which may be extruded or machined, such as e.g. PE, PP, PTFE, gold, silver, titanium, diamond, etc.

The square rod 21 has a length of around 19.4 mm and a cross-section of approximately 2.88 mm×2.88 mm.

The square rod 21 transmits the rotary motion of the motor to the drive shaft. The square rod 21 may have any desired geometrical form which permits a statically determined force application.

The square rod 21 is held by an axial recess 22.1 within a rotation-symmetric clutch element 22, with the ability to slide axially (FIG. 23). By this means it is able to compensate for differences in length in the axial direction (FIG. 18). The recess 22.1 is formed by a larger central bore and four smaller bores arranged along the periphery of the central bore. The bores may be made by drilling, erosion, ultrasonic drilling, laser drilling or water-jet drilling.

The arrangement of the bores provides four double stop edges running axially. The recess 22.1 is provided within a cylindrical section 22.2 of the clutch element 22 and extends from the distal end of the clutch element 22 until shortly before a disc-shaped proximal section 22.3 of the clutch element 22.

The cylindrical section 22.2 has an outside diameter of around 8 mm and the disc-shaped proximal section 22.3 has an outside diameter of approximately 18 mm.

The recess 22.1 is made in such a way that the square rod 21 is held fixed radially and in the peripheral direction, and able to slide axially. The radial fixing of the square rod 21 is effected through the contact of all four longitudinal edges of the square rod 21 with one each of the four double stop edges of the recess 22.1. Axial movement of the square rod 21 in the recess 22.1 results in only minimal friction at the corresponding lines of contact.

It is also possible to provide more or less stop edges. Instead of a square rod it is possible to provide e.g. a triangular or five-sided rod or a profiled rod with any desired cross-sectional surface remaining constant in the longitudinal direction of the rod. The recess 22.1 should be matched in shape to the cross-sectional surface of the profiled rod.

At the distal end and at the periphery of the cylindrical section 22.2 of the clutch element 22, a shoulder 22.4 is formed. Mounted on this shoulder 22.4 is a second inner ring magnet 20.2. The shoulder 22.4 accommodates the inner ring magnet 20.2 in such a way that its outer surface lies flush with the cylindrical surface of the cylindrical section 22.2. This forms, in combination with the outer ring magnet 20.1 similarly encompassing it in the bearing section 19.9 of the clutch housing 19, a magnet ring bearing 20.3.

In the magnet ring bearing 20.3, the two ring magnets 20.1, 20.2 are so arranged that e.g. the north pole of the outer ring magnet is oriented towards the distal end and the south pole towards the proximal end. The north and south poles of the inner ring magnets are correspondingly opposite one another. Similarly, the north and south poles of the two ring magnets could also be reversed. The magnet ring bearing 20.3 centres the drive shaft 4 axially and radially. The radial centering is effected through the radial attraction forces in the radial direction. The axial centering is effected by means of magnetic restoring forces generated by a slight offset of the inner ring magnet 20.2, which pull the inner ring magnet 20.2 into a position coinciding axially with the position of the outer ring magnet 20.1. With a greater offset, however, repelling forces occur between the two magnet rings 20.1 and 20.2, causing them to be pressed apart.

In the magnet ring bearing 20.3 the ring magnets 20.1, 20.2 are not in contact, i.e. no lubrication is required. In addition, the magnet ring bearing acts as a vibration damper.

Formed in the disc-shaped section 22.3 of the magnetic clutch element 22 at the proximal end of the clutch element is a magnet mounting 22.5. The magnet mounting 22.5 is a centric circular recess.

The centric circular recess 22.5 has a diameter of approximately 16.5 mm and a depth of around 3 mm.

The magnet mounting 22.5 accommodates the annular distal magnet unit 23.1 comprised of four segments. The annular distal magnet unit is glued into the magnet mounting 22.5.

Formed centrally in the proximal end face of the clutch element 22 is a ball head bearing mount 22.7. The ball head bearing mount 22.7 is a roughly hemispherical recess 22.7.

The hemispherical recess 22.7 has a diameter of approximately 0.5 to 1.3 mm.

The square rod 21 and the cylindrical section clutch element 22 respectively are held by the fourth bore section 19.8 and the bearing section 19.9 of the clutch housing 19. The disc-shaped section 22.3 of the clutch element 22 is held by the distal clutch section 19.10 of the clutch housing 19.

The clutch housing 19 is separated hermetically from the motor assembly by a terminating disc 24 (FIG. 19). The clutch housing 19 has a gas- and fluid-tight seal apart from the rinsing bore 19.15 in the clutch element 22 and the open spaces between the drive shaft passage section 19.7 and the drive shaft 4.

The terminating disc 24 is mounted on the shoulder 19.12 of the clutch housing 19 and is fixed by means of eight screws, suitably held by bores 24.1 arranged with radial symmetry in the terminating disc 24, and screwed into the tapped holes 19.13 of the clutch housing 19. This connection is fluid- and gas-tight. The terminating disc 24 is made for example of polymethylacrylate (PMMA) or another non-metallic material (e.g. PEEK, PEBAX, Teflon, PP, PE, all non-magnetic materials which can be injection-moulded, extruded or machined).

On the distal side, the terminating disc 24 has a central thicker section 24.2. Formed in the centre of the terminating disc 24 is a through bore 24.3 and a centric hemispherical recess 24.4. Fixed in the through bore 24.3 is a cylindrical centering pin 24.5 (FIG. 21). Mounted on the centering pin 24.5 is a ball head 24.6 which is held in the hemispherical recess (FIG. 15, FIG. 20).

The distal magnet unit 23.1 is biased by a force towards the proximal. These opposing forces produce a resultant force which presses the clutch element 22 against the ball head 24.6. This resultant force is set so that the ball head 24.6 is supported securely, while at the same time wear in the ball head bearing is kept to a minimum.

In combination with the distally located ball head bearing mount 22.7 of the clutch element 22, the ball head 24.6 forms a ball head bearing 25. The ball head bearing 25 is a sliding bearing. Other sliding bearings, such as e.g. a conical head bearing or a cylinder head bearing are also possible, with a cone or a cylinder provided as bearing body instead of the ball. The mounting is suitably matched to the shape of the bearing body.

In conjunction with the magnet ring bearing 20.3, the ball head bearing 25 provides axial centering and guidance, within the clutch housing 19, of the clutch element 22 and the drive shaft 4 mounted within it.

The axial centering of the magnet ring bearing 20.3 is effected by providing that the inner ring magnet 20.2 is mounted axially not exactly in the centre of the outer ring magnet 20.1, but slightly offset to the proximal side. By this means, the inner ring magnet 20.2 is biased towards the distal side. The ball head 24.6 may be made of ruby, aluminium oxide or a rigid plastic.

To prevent blood and serum from being sucked in through the open spaces between the drive shaft 4 and the proximal rotor bearing 17.2, due to the rotary movement of the drive shaft 4, and the blood coagulating and/or adhering to the drive shaft 4, a rinsing medium is introduced through the rinsing bore in the clutch housing to generate a counter-pressure to the sucked-in or pressed-in blood flow. By this means the ball head bearing is lubricated. Suitable rinsing agents are e.g.: 3-20% glucose solution, 5-40% dextrane solution with a molar weight of 5,000 to 65,000, in particular 10% dextrane solution, molar weight 40,000 in 0.9% NaCl Ringer's solution: an electrolyte mixture solution with K, Na, Mg or other physiological electrolyte solutions.

The motor assembly comprises the proximal magnet unit 23.2, a proximal magnet mounting 26, a coupling flange 27, a motor mounting 7.1, with a cooling fan mounted thereon and the motor 7 (FIG. 14. FIG. 22).

On the proximal side of the terminating disc 24, at a distance of roughly 0.5 to 8 mm and preferably around 1 to 2 mm, there is a proximal magnet unit 23.2 mounted axially flush with the distal magnet unit 23.1. Like the distal magnet unit 23.1, the proximal annular magnet unit 23.2 has four segments.

The magnet mounting 26 is disc-shaped and has a centric circular recess 26.1 on its distal side. Bonded into the recess 26.1 by means of two-component epoxy resin or cyanacrylate adhesives are, as in the distal magnet unit 23.1 (see above), four magnet segments.

The four segments of the distal and proximal magnet units 23.1, 23.2 may be in the form of bent bar magnets, each with different poles at their end sections. The four segments may also be in the form of short axially aligned bar magnets, arranged in a ring. It is also possible to provide more than four segments. In the original position the two magnets are arranged so that in each case one north and one south pole of the bar magnets of the two magnet units 23.1, 23.2 overlap and attract one another.

The four segments are arranged four times with their north and south poles alternating on impact, so that the segments attract one magnetic unit. The distal and proximal magnet units 23.1, 23.2 are arranged relative to one another so that in each case complementary poles lie opposite one another. By this means the two magnet units attract one another and a torque is transmitted, since the magnetic forces wish to maintain this complementary pole configuration.

The centric circular recess 26.1 has a diameter of around 16.5 mm and a depth of around 3 mm.

The magnet mounting 26 is connected to a motor shaft 7.2 of the motor 7. The magnet mounting 26 is mounted rotatably within a suitably formed recess of the coupling flange 27 of the motor mounting. Provided along the outer periphery of the annular web of the recess are three dowel pins 27.1, evenly spaced.

The clutch housing 19 is connected to the dowel pins 27.1 of the coupling flange 27 of the motor assembly via the L-shaped recesses 19.14 of the clutch housing 19.

The coupling flange 27 is fastened to a distal end face 7.1.1 of the motor mounting, while maintaining axial symmetry. The motor mounting 7.1 is a rectangular body with cooling fins 7.1.3 provided on its side faces 7.1.2.

In the axial direction, the motor mounting 7.1 has a centrally located bore 7.1.4, through which the motor shaft 7.2 is guided. Also provided is an axially flush recess 7.1.5 in which the motor 7 is fitted.

The motor 7 is for example a standard electric motor from the company Faulhaber with an output of 38 W at 30,000 rpm, or any other suitable motor.

A cooling fan is provided on one side face 7.1.2 of the motor mounting 7.1.

Provided over the pump head 3 and a distal section of the proximal catheter body element is a cover hose 29. The cover hose 29 has an inside diameter which, in the area of the pump head 3, corresponds to the outside diameter of the unexpanded pump housing. The outside diameter of the cover hose is approximately 3 mm.

The method of coupling with the magnetic clutch 9 is now described below.

The two magnet units 23.1, 23.2 are separated physically from one another by the terminating disc 24 in the clutch housing 19. A non-positive connection is created by the magnetic attraction forces between the two magnet units 23.1, 23.2. Here the respectively opposite poles of the two magnet units 23.1, 23.2 are opposite one another, so that they attract one another and a torque-resistant non-positive connection is formed.

Also by this means the ball head bearing mount 22.7 of the clutch element 22 is pressed on to the ball head 24.6 of the terminating disc 24 to form the ball head bearing 25. The ball head bearing centres the axial course of the drive shaft 4.

Through the arrangement of the two ring magnets 20.1, 20.2 of the magnet ring bearing 20.3, the inner ring magnet 20.1 is guided radially in the outer ring magnet 20.2 with constant clearance. In this way the magnet ring bearing 20.3, in combination with the ball head bearing 25, centres and guides the rotation-symmetric motion of the clutch element 22 and the drive shaft 4 respectively, in order to prevent any impact or imbalance.

Via the non-positive connection between the magnet units 23.1, 23.2, the rotary motion transmitted by the motor 7 via the motor shaft 7.2 to the proximal magnet unit 23.2 is transferred to the distal magnet unit 23.1.

The motor shaft 7.2 rotates at a speed of around 20,000 rpm to 40,000 rpm and preferably around 32,000 rpm to 35,000 rpm, which is transmitted to the drive shaft 4. At 32,000 rpm the rotor 3.2 has a pump performance of approximately 2 l/min to 2.5 l/min at a differential pressure of 60 mm Hg.

In the event of jamming of the rotor 3.2, the non-positive connection between motor 7 and drive shaft 4 must be broken, to prevent "winding-up" of the drive shaft 4 while the rotor is stationary. "Winding-up" of the drive shaft 4 could lead to a change in position of the pump head 3, resulting in damage to the heart and/or the aorta and veins.

As soon as the rotor 3.2 jams, the drive shaft 4 twists and shortens, and the resistance at the distal magnet unit 23.1 increases. The magnetic fields between the proximal and the distal magnet units 23.2, 23.1 do not overlap completely in operation, since the distal magnet unit 23.1 always trails the proximal magnet unit 23.2 a little. If now the torque required at the distal magnet unit 23.1 increases, the north and south poles of the magnet units 23.1, 23.2 no longer overlap but instead abut one another. By this, the distal magnet unit 23.1 is pressed away from the proximal magnet unit 23.2 in the distal direction. The magnetic connection between the two magnet units 23.1, 23.2 is broken and the drive shaft 4 comes immediately to a stand.

Due to the displacement of the clutch element 22 in the distal direction, the inner ring magnet 20.2 of the clutch element 22 is similarly shifted in the distal direction and the north and south poles of the two ring magnets 20.1, 20.2 of the magnet ring bearing 20.3 no longer overlap but instead abut one another. By this means, the clutch 9 is held in the decoupled state, resulting in a lasting decoupling of motor 7 and drive shaft 4.

The amount of transferable torque is limited by the magnet ring bearing 20.3 and the magnetic connection of the two magnet units 23.1, 23.2. As soon as the set torque is exceeded, the two magnet units 23.1, 23.2 separate. Owing to the rapid rotary motion, the distal magnet unit 23.1 can no longer follow the proximal magnet unit 23.2, since the magnetic binding forces are no longer adequate. Because of this, the north and south poles no longer overlap and the magnet units 23.1, 23.2 repel one another. The connection of the magnet units 23.1, 23.2 is broken and the maximum transferable torque is limited. The magnet units 23.1, 23.2 are held in the decoupled state by the magnet ring bearing 203 through the mutual repulsion of the ring magnets 20.1, 20.2.

This state may be changed again by the application of an outer magnetic field. By means of a magnet guided past the clutch housing 19 from distal to proximal, the two magnet units 23.1, 23.2 may be brought back into their coupled original position.

According to the invention the clutch housing 19 and the motor assembly 30 are physically separated from one another. Because of this it is possible to lubricate the drive shaft 4 through the pump located at the rinsing bore 19.15, at around 5-10 ml/h, despite the high speed, thereby minimising friction. It may also be provided for an infusion to be made via the rinsing bore 19.15, which similarly lubricates the drive shaft 4.

The small diameter of the drive shaft is advantageous at high speeds of around 32,000 rpm. With greater diameters the peripheral speed would be too high and the friction could lead to damage to the drive shaft 4 and the adjacent components.

On account of the physical separation by the terminating disc 24 it is possible to lubricate and/or seal the drive shaft 4. No known bearing through which a shaft is guided would remain leak-proof and allow trouble-free running with this size and at such speeds.

The arrangement of the ball head bearing 25 (sliding bearing), the magnet ring bearing 20.3 (non-contact, damping and centering) and the axial sliding bearing between the drive shaft 4 and the clutch housing 19 creates three stabilisation points. This enables the drive shaft 4 to transmit a torque even if there is an axial change in length (lengthening and shortening). A change in length occurs, for example, when the pump head 3 is compressed. Here the rotor 3.2 is pressed together, folded around the drive shaft and clamped in place in the housing. The pump housing 3.1 extends to the proximal side. The drive shaft 4 is able to move sufficiently for it not to be torn away from the rotor 3.2. The ability of the drive shaft 4 to slide makes it possible to compensate for change in length of the PU catheter body due to take-up of liquid, variations in temperature, and bending of the proximal catheter body element 8.2, which affect the length relationships between drive shaft 4 and proximal catheter body element 8.2. This mechanism is possible because of the ability of the square rod 21 to slide within the axial recess 22.1.

The pump head 3 is located in the left-hand heart chamber in such a way that the outlet hose 18 is arranged roughly centrally in the transition from the aorta to the heart, i.e. in the area of the heart valve. The catheter device 1 is preferably designed so that a certain pump pressure in the range of around 100 mm Hg to 150 mmHg may be obtained from it. If the heart is in the systole, then the catheter device pumps blood when the pressure built up by the heart is less than the pump pressure. A sick heart is thus relieved of stress. During the diastole, the pressure difference is opposite. If the pressure difference is greater than the pump pressure, then the catheter device can not pump blood. In this case the outlet hose is pressed together by the heart valve, so that it is closed. If however the pressure difference is less than the pump pressure, then some blood will be pumped against the pressure difference.

FIG. 24 shows the catheter device 1 positioned to give left-side support to the heart. The pump head 3 is located completely in the left heart chamber. The outlet hose extends through the heart valve.

To insert the catheter device, firstly a cover hose 29 is guided by a guide wire into the left heart chamber (Seldinger technique). The guide wire is then removed from the cover hose. The catheter device 1 is inserted through the cover hose with compressed and cooled pump housing 19 and rotor 3.2 until the catheter device 1 with the pump head 3 has reached the left heart chamber. Unfolding takes place through the pulling back of the cover hose 29 on to the fixed catheter body 8, until the tip of the cover hose 29 has released the pump head 3.

To remove the system, the cover hose 29 is pushed forward up to the body cap 10, causing the rotor 3.2 and pump housing 3.1 to be drawn into the cover hose 29 in the compressed state, after which the cover hose is extracted through the puncture point.

In a further embodiment of the present invention, provision is made for a pump medium to be pumped from proximal to distal, i.e. against the original flow direction 5 (FIG. 25 II). To support the rotor 3.2 in the axial direction and to absorb the bearing forces, the bearing washer 15 is provided on the proximal side of the rotor 3.2. The flow direction to the distal side may be obtained either by reversing the direction of rotation from that of the embodiment above, or by inverting the pitch of the rotor 3.2. The outlet hose 18 is located at the distal end of the pump section of the clutch housing 19 and extends beyond the pump head in the distal direction. To reinforce the outlet hose 18 it may have a mesh structure of a memory material e.g. similar to that of the pump housing. The body cap 10 extends beyond the distal end of the outlet hose.

In operation, the pump medium flows into the pump housing through the pump housing outlets now serving as inlets, and passes into the outlet hose 18 through the pump housing inlet now serving as the outlet. The pump medium passes out of the catheter device 1 through the distal end of the outlet hose.

The embodiment just described may be provided for example for use in the right ventricle.

In a further embodiment, the catheter device according to the invention may also be designed so that pumping from distal to proximal and from proximal to distal is possible (FIG. 25 III).

In this embodiment, bearing washers 15 are provided at the distal and proximal ends of the rotor 3.2. The outlet hose 18 is located at the distal end of the pump section 3.1.3 of the pump housing 3.1 and extends in the distal direction. For reinforcement, the outlet hose 18 has a mesh structure, e.g. similar to that of the pump housing. The mesh structure is covered by a PU skin. The diameter of the outlet hose 18 corresponds roughly to that of the expanded pump housing.

In operation a pump medium may enter or exit through the outlets of the pump housing. The pump medium then passes for example via the outlets of the pump housing and the inlets of the pump housing into the outlet hose, and exits at the distal end of the outlet hose. With the direction of pumping reversed, the flow through the catheter device is correspondingly reversed. This means that the pump medium enters the outlet hose at the distal end of the outlet hose, and arrives at the outlets of the pump housing via the inlets of the pump housing. Consequently, a flow to distal or proximal is possible through the pressure- and suction-stabilised outlet hose 18.

The embodiment just described may be used for example for drainage or filling of hollow organs or spaces.

The reversed direction of flow may be obtained on the one hand by reversing the direction of rotation of the rotor and on the other hand by inverting the pitch of the rotor.

The invention is described above with the aid of an embodiment in which the magnet units each have four bent bar magnets, each placed next to one another with opposite poles. Within the scope of the invention however the magnet units may also be so designed that the north and south poles of the magnet units are oriented in the axial direction, wherein the poles are provided on the axial surfaces facing the distal or proximal end. The magnets are arranged in a ring as in the previous embodiments.

Through such an alignment of the north and south poles of the magnets, the two magnet units attract with greater magnetic forces. By this means it is possible to transmit a higher torque via the clutch.

A clutch of this kind may be used for example to drive a milling head instead of a rotor. Using such a micro-miller, e.g. kidney stone or bones may be milled with minimal invasion.

The number of magnets may in principle be varied as desired.

The radial compressibility of the components makes it possible to realise a very small puncture diameter, suitable for percutaneous implantation by the Seldinger technique, on account of the very small diameter of the catheter device, amounting to approximately 3 mm. Due however to the expansion of the rotor up to a diameter of around 15 mm, it is still possible to obtain very high pump performance.

Known from the prior art are expandable catheter pumps (e.g. U.S. Pat. No. 4,753,221) which have a propeller with several rigid pump blades. These are mounted pivotably. Since the blades are rigid, they can not be made as wide as desired since, in the folded state, they would require a catheter which was too thick. Pump performance is therefore limited.

The rotor according to WO 99/44651 has an elastic band for connecting a nitinol filament to a rotation axis. Because of this elastic connection, the filament is not perfectly centred. During pumping, this can lead to vibrations which make higher speeds or rates of pumping impossible.

Because of the frame structure of the rotor with boundary frame and rotor struts in accordance with the catheter device 1, the rotor is more stable, capable of folding and of expansion to virtually any diameter required. Due to the fact that the rotor may be virtually as long as desired in the axial direction, the radial extent of the rotor may be chosen freely. This makes it possible to obtain virtually any level of pump performance, in particular very high performance, and it is possible to adapt pump performance specifically for each application.

The pitch of the rotor may also be varied as desired. The rotor may be designed with one or several rotor blades, with the rotor blades accordingly having a quarter, a half a whole or as many twists around the drive shaft as desired. This means that the rotor may be varied as desired in its size, shape and pitch, and may therefore be used for the most diverse applications.

LIST OF REFERENCE NUMBERS 1 catheter device
2 distal end
3 pump head
3.1 pump housing
3.1.1 distal connection section
3.1.2 intake section
3.1.3 pump section
3.1.4 outlet section
3.1.5 proximal connection section
3.1.6 mesh structure
3.1.7 apertures
3.1.7.1 small rhombus
3.1.7.2 large rhombus
3.1.7.3 medium-sized rhombus
3.1.8 PU covering of the pump housing
3.2 rotor
3.2.1 frame structure
3.2.2 boundary frame
3.2.3 rotor struts
3.2.4 rings
4 drive shaft
4.1 distal section of the drive shaft
4.2 pump section of the drive shaft
4.3 proximal section of the drive shaft
5 flow direction
6 proximal end
7 motor
7.1 motor mounting
7.1.1 end face
7.1.2 side face
7.1.3 cooling fins
7.1.4 bore
7.1.5 recess
7.2 motor shaft
8 catheter body
8.1 distal catheter body element
8.2 proximal catheter body element
9 clutch
10 body cap
10.1 ball
10.2 cylindrical section
10.3 through bore
10.4 axial bore
10.5 step
12.1 distal connection bush
12.2 proximal connection bush
13.1 distal shaft protector
13.2 proximal shaft protector
14 guide spiral
15 bearing washer
15.1 through bore
16 spacer sleeves
17 distal rotor bearing
18 outlet hose
18.1 outlet
19 clutch housing
19.1 distal cylindrical section
19.2 conically widening section
19.3 second cylindrical section
19.4 proximal cylindrical section
19.5 catheter body mounting section
19.6 guide spiral mounting section
19.7 drive shaft passage section
19.8 fourth bore section
19.9 bearing section
19.10 distal clutch section
19.11 proximal clutch section
19.12 shoulder
19.13 tapped hole
19.14 L-shaped recess
19.15 rinsing bore
20.1 outer ring magnet
20.2 inner ring magnet
20.3 magnet ring bearing
21 square rod
21.1 recess
22 clutch element
22.1 recess
22.2 cylindrical section
22.3 disc-shaped section
22.4 shoulder
22.5 magnet mounting
22.6 ball head bearing mount
23.1 distal magnet unit
23.2 proximal magnet unit 24 terminating disc
24.1 bores
24.2 thicker sections
24.3 through bore
24.4 hemispherical recess
24.5 centering pin
24.6 ball head
25 ball head bearing
26 magnet mounting
26.1 recess
27 coupling flange
27.1 dowel pins
28
29 cover hose
30 motor assembly That which is claimed:

1. A percutaneous heart pump system being configured for percutaneous insertion through a vascular system of a patient and positioning across an aortic valve, comprising:
    a catheter having a tubular pump housing disposed at a distal portion of the catheter, the pump housing having distal inlet holes and proximal outlet holes and a tubular fluid flow surface that extends between the inlet and outlet holes and forms a contact interface for positioning across the aortic value;
    a radially compressible helical rotor disposed within the pump housing, wherein the rotor includes a central bore;
    a drive shaft disposed within the pump housing and having a proximal drive shaft portion and a distal drive shaft portion, wherein the proximal drive shaft portion is configured to couple to a motor and the distal drive shaft portion extends through the central bore of the rotor and is configured to rotate the rotor within the pump housing;
    a body cap having a distal tip and a proximal opening; and
    a distal bearing section positioned axially along the drive shaft at a position distal to the rotor, the distal bearing section comprising a tubular distal shaft protector having a central bore, the central bore comprising:
        a proximal opening,
        a distal opening, and
        an interior cylindrical surface that surrounds the distal portion of the drive shaft;
    wherein the drive shaft extends through the distal shaft protector and into the proximal opening of the body cap.

2. The system of claim 1, wherein the distal shaft protector has a cylindrical surface axially aligned with the drive shaft.

3. The system of claim 2, wherein the pump housing comprises a self-expanding mesh tube configured to expand from a collapsed state to an expanded state, and the distal shaft protector is disposed within the mesh tube.

4. The system of claim 3, wherein the distal bearing section includes a distal support that extends radially about the distal shaft protector and the drive shaft.

5. The system of claim 4, wherein the radially extending distal support contacts the mesh tube.

6. The system of claim 5, wherein the radially extending distal support centers the drive shaft within the mesh tube in the expanded state of the mesh tube.

7. The system of claim 6, wherein the radially extending distal support has a proximal region with a first diameter and a distal region with a second diameter.

8. The system of claim 7, wherein the first diameter is smaller than the second diameter.

9. The system of claim 8, wherein the radially extending distal support comprises a cylindrical connection bush.

10. The system of claim 3, wherein the mesh tube is surrounded by a substantially liquid-proof seal.

11. The system of claim 3, wherein the rotor is formed from an elastic material such that the rotor automatically unfolds when released from the mesh tube.

12. The system of claim 11, wherein the rotor comprises a continuous helical rotor blade having a length.

13. The system of claim 12, wherein a pitch of the continuous helical rotor blade varies along the length of the blade.

14. The system of claim 2, wherein the rotor is coupled to the drive shaft by a rotor connector.

15. The system of claim 14, wherein the rotor connector comprises a non-positive connector.

16. The system of claim 14, wherein the rotor connector comprises a clamp.

17. The system of claim 2, wherein the distal bearing section comprises a sliding distal bearing.

18. The system of claim 1, wherein the body cap is distal of the pump housing.

19. The system of claim 18, wherein the body cap comprises a distal atraumatic ball.

20. The system of claim 19, wherein the distal atraumatic ball is configured to space the pump housing from an interior wall of the patient's vessel.

* * * * *